(12) United States Patent
Tanabe et al.

(10) Patent No.: US 12,343,099 B2
(45) Date of Patent: Jul. 1, 2025

(54) ROBOTIC SURGICAL SYSTEM, OPERATOR-SIDE APPARATUS, AND CONTROL METHOD OF ROBOTIC SURGICAL SYSTEM

(71) Applicant: KAWASAKI JUKOGYO KABUSHIKI KAISHA, Kobe (JP)

(72) Inventors: Masataka Tanabe, Kobe (JP); Yusuke Takano, Kobe (JP); Takeshi Kurihara, Kobe (JP); Shinji Kajihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 411 days.

(21) Appl. No.: 17/832,759

(22) Filed: Jun. 6, 2022

(65) Prior Publication Data

US 2022/0387120 A1     Dec. 8, 2022

(30) Foreign Application Priority Data

Jun. 8, 2021   (JP) .................................. 2021-096094

(51) Int. Cl.
*A61B 34/00* (2016.01)
*A61B 34/37* (2016.01)
*B25J 9/16* (2006.01)
*A61B 34/30* (2016.01)

(52) U.S. Cl.
CPC .............. *A61B 34/37* (2016.02); *A61B 34/77* (2016.02); *B25J 9/1633* (2013.01); *A61B 2034/254* (2016.02); *A61B 2034/306* (2016.02)

(58) Field of Classification Search
CPC ............. B60W 10/18; B60W 2710/18; B60W 2050/0026; B60W 2050/0095; A61B 34/30; A61B 2090/508; A61B 34/37; A61B 2090/031; A61B 6/0487; B60T 8/172; B60T 2201/03; B25J 19/0004; B25J 9/1674; B25J 9/0084; G05B 2219/41279; G05B 2219/41285; G05B 2219/42284; G05B 19/41805; G05B 2219/43064; G05B 2219/40205; G05B 2219/40202

See application file for complete search history.

(56) References Cited

U.S. PATENT DOCUMENTS

| | | |
|---|---|---|
| 2003/0191454 A1 | 10/2003 | Niemeyer |
| 2004/0243110 A1 | 12/2004 | Niemeyer |
| 2014/0135795 A1 | 5/2014 | Yanagihara |
| 2014/0297130 A1* | 10/2014 | Griffiths ................. A61B 50/13 701/41 |
| 2016/0377508 A1* | 12/2016 | Perrone .................. G01M 17/06 180/204 |
| 2017/0079731 A1* | 3/2017 | Griffiths ................. A61B 34/30 |

(Continued)

FOREIGN PATENT DOCUMENTS

| | | |
|---|---|---|
| EP | 3342543 A1 | 7/2018 |
| JP | 2013-034830 A | 2/2013 |

(Continued)

*Primary Examiner* — Darrin D Dunn
(74) *Attorney, Agent, or Firm* — METROLEX IP LAW GROUP, PLLC; Robert L. Scott, Esq.

(57) ABSTRACT

In a robotic surgical system, an operation unit includes a drive to assist an operation of an operator. A controller is configured or programmed to control the drive to exert a braking force when the operation on the operation unit is decelerated and/or accelerated.

16 Claims, 16 Drawing Sheets

(56) References Cited

U.S. PATENT DOCUMENTS

| | | | |
|---|---|---|---|
| 2018/0326852 A1* | 11/2018 | Shiozawa | B60L 9/18 |
| 2020/0298855 A1* | 9/2020 | Demerly | B60W 30/143 |
| 2021/0086374 A1* | 3/2021 | Brandt | B25J 9/1674 |
| 2022/0410720 A1* | 12/2022 | Tessaro | B60L 15/2009 |
| 2023/0356601 A1* | 11/2023 | Yamamoto | B60L 7/26 |
| 2024/0268911 A1* | 8/2024 | Wang | A61B 34/30 |

FOREIGN PATENT DOCUMENTS

| | | |
|---|---|---|
| JP | 2021-023705 A | 2/2021 |
| WO | 98/08159 A2 | 2/1998 |

* cited by examiner

DURING DECELERATION

ROBOTIC SURGICAL SYSTEM, OPERATOR-SIDE APPARATUS, AND CONTROL METHOD OF ROBOTIC SURGICAL SYSTEM

CROSS-REFERENCE TO RELATED APPLICATION

The present application claims priority to JP2021-096094, which is incorporated herein by reference.

BACKGROUND OF THE INVENTION

Field of the Invention

The present disclosure relates to a robotic surgical system, an operator-side apparatus, and a control method of a robotic surgical system, and more particularly, it relates to a robotic surgical system and an operator-side apparatus each including an operation unit to receive an operator's operation, and a control method of the robotic surgical system.

Description of the Background Art

Conventionally, a robotic surgical system including an operation unit to receive an operator's operation is known. For example, a technology that controls movement of a surgical instrument provided on an articulated robot arm as a slave based on the amount of operation received by an operation unit provided in a master control device is disclosed in U.S. Patent Application Publication No. 2004/0243110. In U.S. Patent Application Publication No. 2004/0243110, a tool moves within the patient's body, which is a surgical site.

In U.S. Patent Application Publication No. 2004/0243110, the operation unit provided in the master control device includes an articulated arm including a plurality of links. The articulated arm is suspended from above while being bent in an L shape. Furthermore, the articulated arm includes a motor. Thus, even when an operator does not support the operation unit by hand, the torque of the motor is generated so as to resist the gravity such that the L-shaped bent state of the articulated arm is maintained.

In U.S. Patent Application Publication No. 2004/0243110, the motor generates a force according to an operation speed at which the operator operates the operation unit so as to compensate for the frictional force of a gear or the like provided between the motor and the master control device. Thus, it is possible to lighten an operator's operation on the operation unit.

However, as in the U.S. Patent Application Publication No. 2004/0243110, when generation of the force in the motor of the articulated arm assists in lightening the operation on the operation unit, the operation unit may not be stopped at an appropriate position intended by the operator. Therefore, it is desired to stop the operation unit of the master control device at the appropriate position.

SUMMARY OF THE INVENTION

The present disclosure is intended to solve the above problem. The present disclosure aims to provide a robotic surgical system, an operator-side apparatus, and a control method of a robotic surgical system each capable of stopping an operation unit of the operator-side apparatus at an appropriate position.

In order to attain the aforementioned object, a robotic surgical system according to a first aspect of the present disclosure includes a patient-side apparatus including a manipulator arm to which a surgical instrument is attached to a tip end of the manipulator arm, an operator-side apparatus including an operation unit to receive an operation of an operator, and a controller. The operation unit includes a drive to assist the operation, and the controller is configured or programmed to control the drive to exert a braking force when the operation on the operation unit is decelerated and/or accelerated.

In the robotic surgical system according to the first aspect of the present disclosure, as described above, the operation unit includes the drive to assist the operation, and the controller is configured or programmed to control the drive to exert the braking force when the operation on the operation unit is decelerated and/or accelerated. Accordingly, the braking force is exerted during deceleration such that overshoot caused by the inertia of the operation unit when an operator tries to stop the operation unit suddenly is significantly reduced or prevented. Furthermore, the braking force is exerted during acceleration such that movement of the operation unit due to a reaction caused when the operation unit is suddenly stopped, for example, is significantly reduced or prevented. Thus, the operation unit of the operator-side apparatus can be stopped at an appropriate position. The overshoot indicates that the operation unit overshoots the appropriate stop position.

An operator-side apparatus according to a second aspect of the present disclosure operates a patient-side apparatus including a manipulator arm to which a surgical instrument is attached to a tip end of the manipulator arm, and includes the operator-side apparatus including an operation unit to receive an operation of an operator, and a controller. The operation unit includes a drive to assist the operation, and the controller is configured or programmed to control the drive to exert a braking force when the operation on the operation unit is decelerated and/or accelerated.

In the operator-side apparatus according to the second aspect of the present disclosure, as described above, the operation unit includes the drive to assist the operation, and the controller is configured or programmed to control the drive to exert the braking force when the operation on the operation unit is decelerated and/or accelerated. Accordingly, the braking force is exerted during deceleration such that overshoot caused by the inertia of the operation unit when an operator tries to stop the operation unit suddenly is significantly reduced or prevented. Furthermore, the braking force is exerted during acceleration such that movement of the operation unit due to a reaction caused when the operation unit is suddenly stopped, for example, is significantly reduced or prevented. Thus, it is possible to provide the operator-side apparatus capable of being stopped at an appropriate position.

A control method of a robotic surgical system including a patient-side apparatus that includes a manipulator arm to which a surgical instrument is attached to a tip end of the manipulator arm and an operator-side apparatus that includes an operation unit to receive an operation of an operator, which includes a drive to assist the operation, according to a third aspect of the present disclosure includes receiving the operation on the operation unit, and controlling the drive to exert a braking force when the operation on the operation unit is decelerated and/or accelerated.

As described above, the control method of the robotic surgical system according to the third aspect of the present disclosure includes controlling the drive to exert the braking force when the operation on the operation unit is decelerated and/or accelerated. Accordingly, the braking force is exerted during deceleration such that overshoot caused by the inertia of the operation unit when an operator tries to stop the operation unit suddenly is significantly reduced or prevented. Furthermore, the braking force is exerted during acceleration such that movement of the operation unit due to a reaction caused when the operation unit is suddenly stopped, for example, is significantly reduced or prevented. Thus, it is possible to provide the control method of the robotic surgical system capable of stopping the operation unit of the operator-side apparatus at an appropriate position.

According to the present disclosure, the operation unit of the operator-side apparatus can be stopped at the appropriate position.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
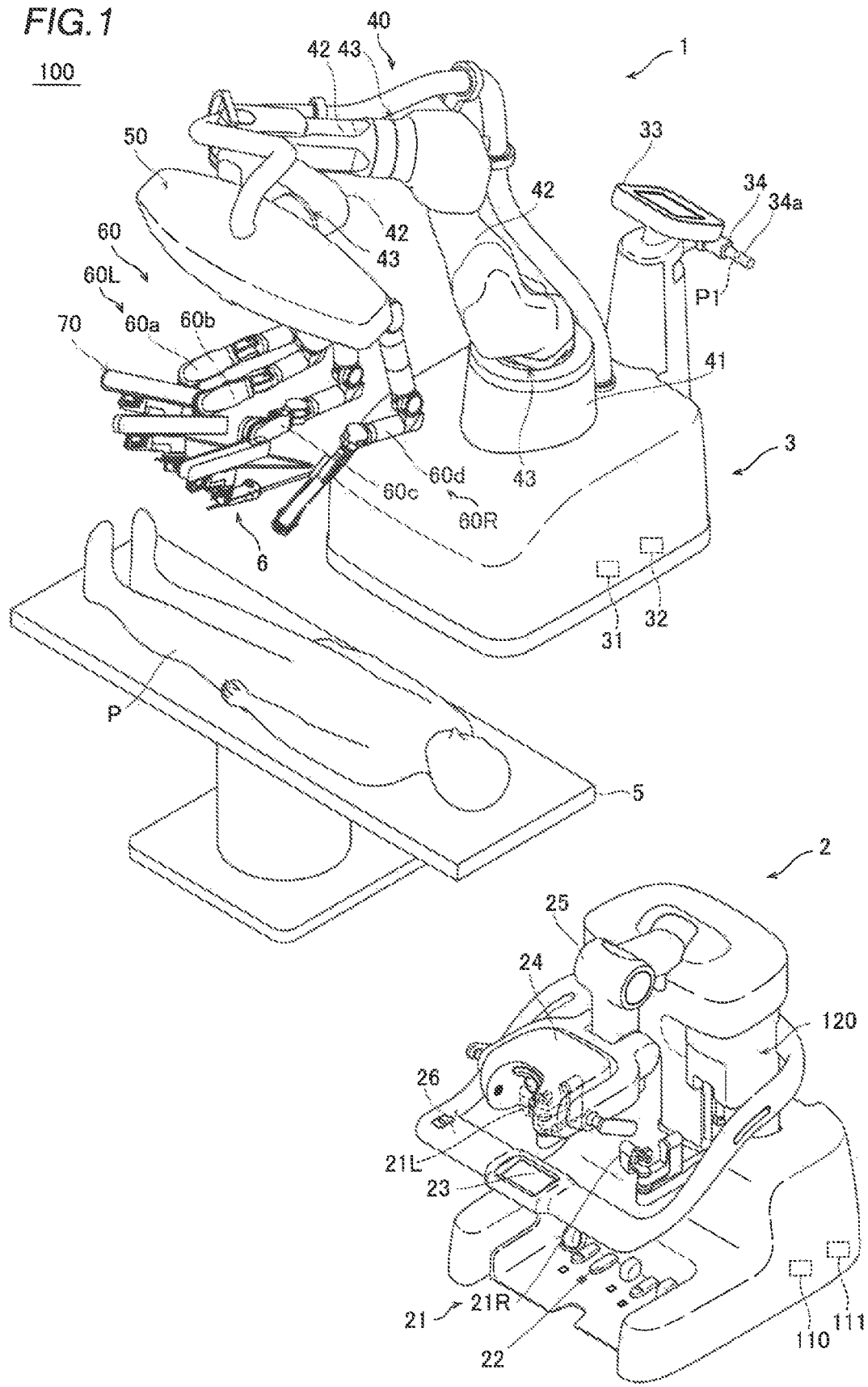
FIG. 1 is a diagram showing the configuration of a surgical system according to a first embodiment.

Embodiments of the present disclosure are hereinafter described with reference to the drawings.

First Embodiment

The configuration of a surgical system 100 according to a first embodiment is now described with reference to FIGS. 1 to 20. The surgical system 100 includes a medical manipulator 1 that is a patient P-side apparatus and a remote control apparatus 2 that is an operator-side apparatus to operate the medical manipulator 1. The medical manipulator 1 includes a medical cart 3 and is movable. The remote control apparatus 2 is spaced apart from the medical manipulator 1, and the medical manipulator 1 is remotely operated by the remote control apparatus 2. An operator such as a doctor inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The surgical system 100 is an example of a robotic surgical system.

The remote control apparatus 2 is arranged inside or outside the operating room, for example. The remote control apparatus 2 includes an operation unit 120 including arms 121 shown in FIG. 3 and an operation handle 21, foot pedals 22, a touch panel 23, a monitor 24, a support arm 25, and a support bar 26. The operation unit 120 includes an operation handle for the operator such as a doctor to input a command.

Figure 3:
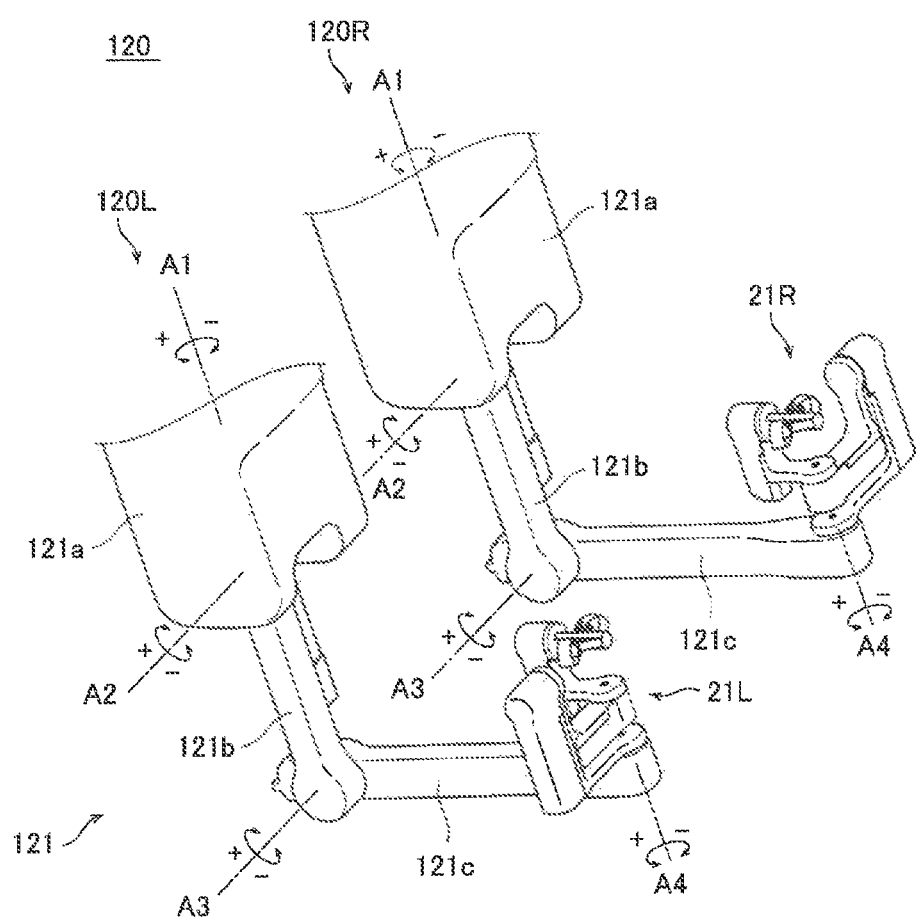
FIG. 3 is a perspective view showing the configuration of an operation unit of a remote control apparatus according to the first embodiment.

As shown in FIG. 3, the operation unit 120 includes an operation unit 120L located on the left side as viewed from the operator such as a doctor and operated by the operator's left hand, and an operation unit 120R located on the right side and operated by the operator's right hand. The configurations of the operation unit 120L and the operation unit 120R are the same as each other.

The operation unit 120 includes the substantially L-shaped arms 121. The arms 121 each have a first link 121a, a second link 121b, and a third link 121c. The upper end side of the first link 121a is attached to a main body of the remote control apparatus 2 such that the first link 121a is rotatable about an A1 axis along a vertical direction. The upper end side of the second link 121b is attached to the lower end side of the first link 121a such that the second link 121b is rotatable about an A2 axis along a horizontal direction. A first end side of the third link 121c is attached to the lower end side of the second link 121b such that the third link 121c is rotatable about an A3 axis along the horizontal direction. The operation handle 21 is attached to a second end side of the third link 121c such that the operation handle 21 is rotatable about an A4 axis.

The arms 121 each support the operation handle 21 such that the operation handle 21 is movable within a predetermined three-dimensional operation range. Specifically, the arm 121 supports the operation handle 21 such that the operation handle 21 is movable in an upward-downward direction, a right-left direction, and a forward-rearward direction. Manipulator arms 60 are moved three-dimensionally so as to correspond to the three-dimensional operations of the arms 121.

The operation handle 21 operates a surgical instrument 4. Furthermore, the operation handle 21 receives an operation amount for the surgical instrument 4. The operation handle 21 includes an operation handle 21L located on the left side as viewed from the operator such as a doctor and operated by the operator's left hand, and an operation handle 21R located on the right side and operated by the operator's right hand.

Figure 4:
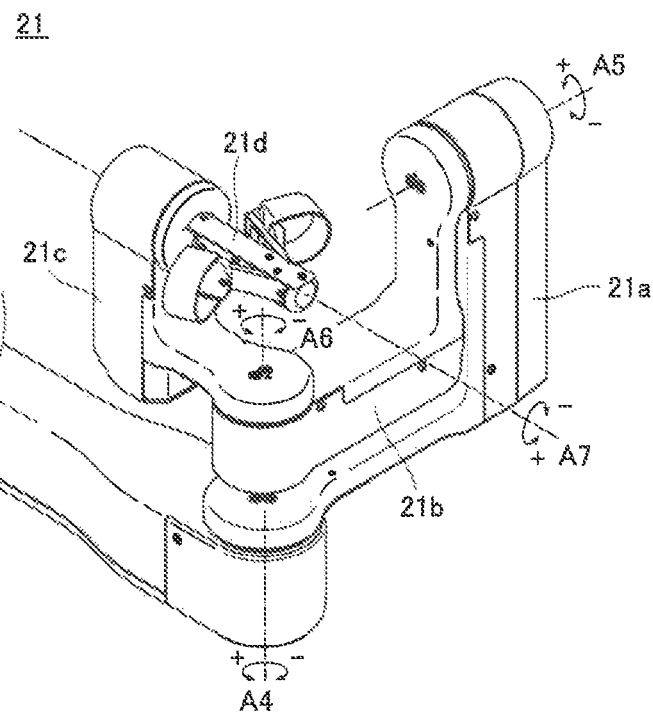
FIG. 4 is a diagram showing the configuration of an operation handle according to the first embodiment.

As shown in FIG. 4, the operation handle 21 includes a link 21a, a link 21b, a link 21c, and a link 21d operated by the operator such as a doctor. The link 21a rotates about the A4 axis. The link 21b rotates about an A5 axis with respect to the link 21a. The link 21c rotates about an A6 axis with respect to the link 21b. The link 21d rotates about an A7 axis with respect to the link 21c.

In the operation handle 21, the movement amounts of the manipulator arms 60 and the surgical instrument 4 are changed with respect to an operation amount received by the operation handle 21. This change is called scaling. For example, when the scale factor of the movement amounts is set to ½ times, the surgical instrument 4 is controlled to move ½ of the movement distance of the operation handle 21. Thus, fine surgery can be performed accurately.

Figure 5:
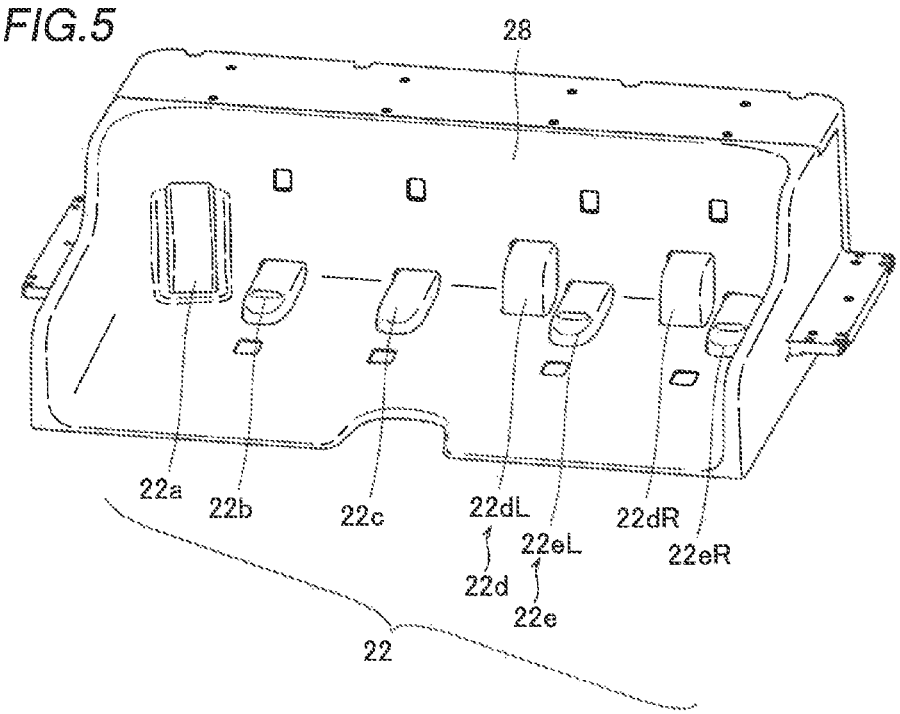
FIG. 5 is a diagram showing the configuration of foot pedals according to the first embodiment.

As shown in FIG. 5, a plurality of foot pedals 22 are provided to perform functions related to the surgical instrument 4. The plurality of foot pedals 22 are arranged on a base 28. The foot pedals 22 includes a switching pedal 22a, a clutch pedal 22b, a camera pedal 22c, an incision pedal 22d, and a coagulation pedal 22e. The switching pedal 22a, the clutch pedal 22b, the camera pedal 22c, the incision pedal 22d, and the coagulation pedal 22e are operated by the operator's foot. The incision pedal 22d includes an incision pedal 22dR for a right manipulator arm 60, and an incision pedal 22dL for a left manipulator arm 60. The coagulation pedal 22e includes a coagulation pedal 22eR for the right manipulator arm 60 and a coagulation pedal 22eL for the left manipulator arm 60.

The switching pedal 22a switches a manipulator arm 60 to be operated by the operation handle 21. In the first embodiment, the clutch pedal 22b performs a clutch operation to temporarily disconnect an operation connection between the manipulator arm 60 and the operation handle 21. While the clutch pedal 22b is being pressed by the operator, an operation by the operation handle 21 is not transmitted to the manipulator arms 60. While the camera pedal 22c is being pressed by the operator, the operation handle 21 can operate a manipulator arm 60 to which an endoscope 6 is attached. While the incision pedal 22d or the coagulation pedal 22e is being pressed by the operator, an electrosurgical device (not shown) is activated.

As shown in FIG. 1, the monitor 24 is a scope-type display that displays an image captured by the endoscope 6. The support arm 25 supports the monitor 24 so as to align the height of the monitor 24 with the height of the face of the operator such as a doctor. The touch panel 23 is arranged on the support bar 26. The operator's head is detected by a sensor (not shown) provided in the vicinity of the monitor 24 such that the medical manipulator 1 can be operated by the remote control apparatus 2. The operator operates the operation handle 21 and the foot pedals 22 while visually recognizing an affected area on the monitor 24. Thus, a command is input to the remote control apparatus 2. The command input to the remote control apparatus 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2.

The medical cart 3 includes an input 33. The input 33 receives operations to move a positioner 40, an arm base 50, and a plurality of manipulator arms 60 or change their postures mainly in order to prepare for surgery before the surgery.

Figure 2:
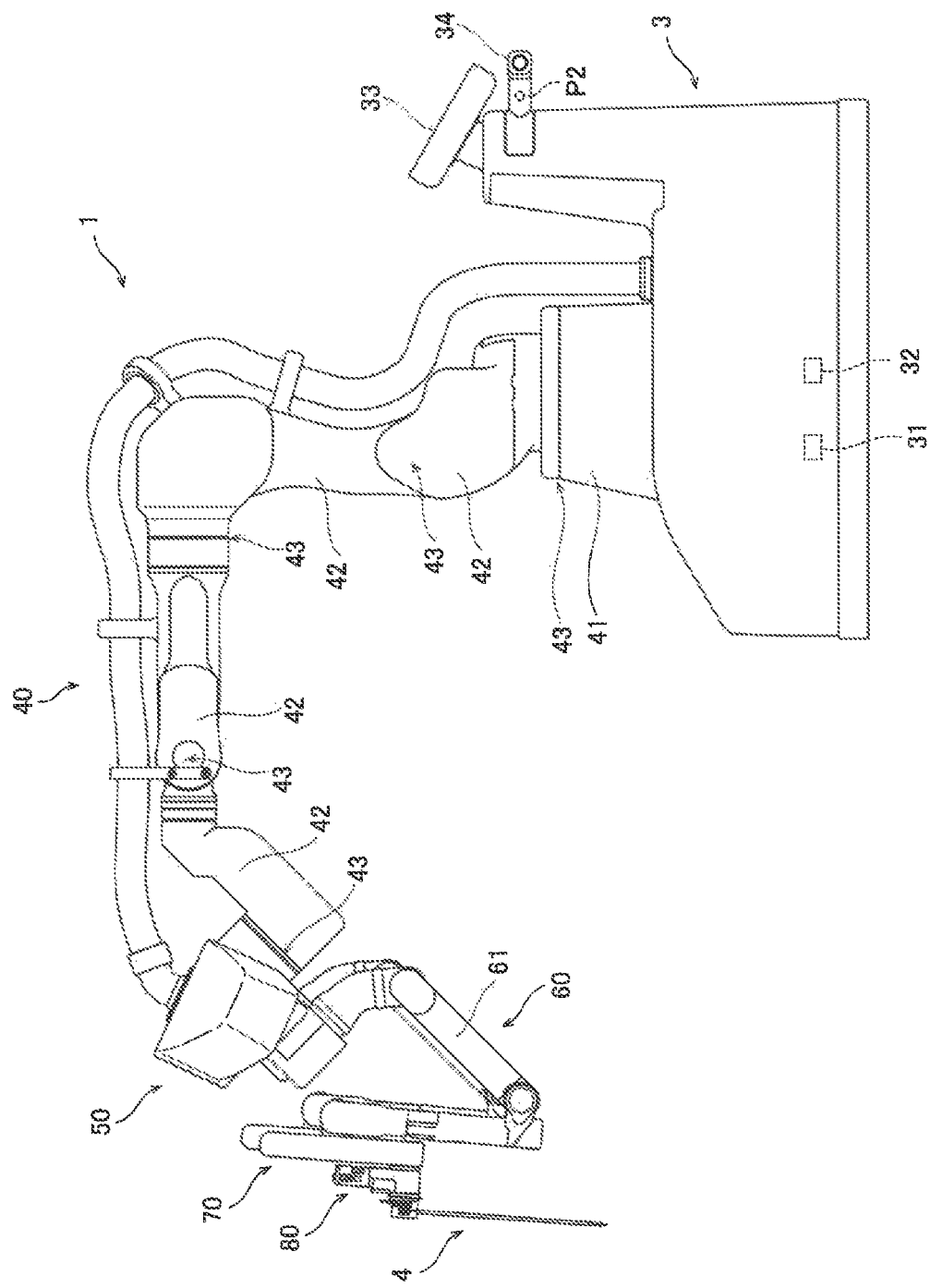
FIG. 2 is a diagram showing the configuration of a medical manipulator according to the first embodiment.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape. That is, the arm base 50 has a long shape. The bases of the plurality of manipulator arms 60 are attached to the arm base 50. Each of the plurality of manipulator arms 60 is able to take a folded and stored posture. The arm base 50 and the plurality of manipulator arms 60 are covered with sterile drapes (not shown) and used. The manipulator arms 60 support the surgical instrument 4.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, the surgical instrument 4 is attached to the tip end of each of the plurality of manipulator arms 60. The surgical instrument 4 includes a replaceable instrument or the endoscope 6 shown in FIG. 9 to capture an image gr of a surgical site, for example.

Figure 6:
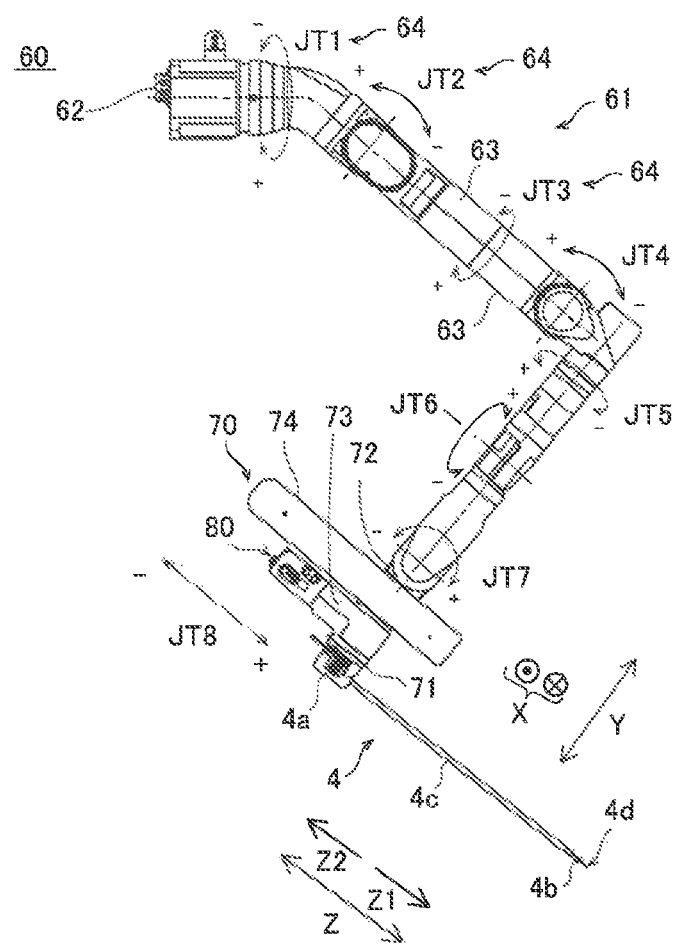
FIG. 6 is a diagram showing the configuration of a manipulator arm according to the first embodiment.

As shown in FIG. 6, the instrument includes a driven unit 4a driven by servomotors M2 provided in a holder 71 of each of the manipulator arms 60. A pair of forceps 4b is provided at the tip end of the instrument.

Figure 7:
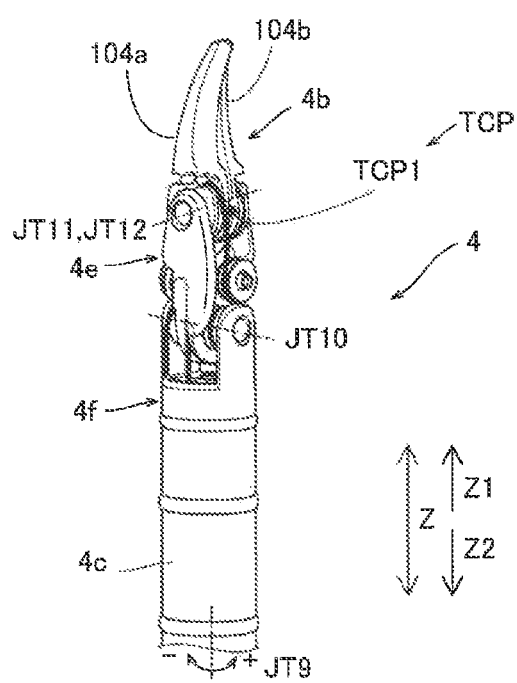
FIG. 7 is a diagram showing a pair of forceps.

As shown in FIG. 7, the instrument includes a first support 4e that supports the base end sides of end effector members 104a and 104b such that the base end sides of the end effector members 104a and 104b are rotatable about a JT11 axis on the tip end sides, a second support 4f that supports the base end side of the first support 4e such that the base end side of the first support 4e is rotatable about a JT10 axis on the tip end side, and a shaft 4c connected to the base end side of the second support 4f. The driven unit 4a, the shaft 4c, the second support 4f, the first support 4e, and the pair of forceps 4b are arranged along a Z direction. The JT11 axis is orthogonal to the Z direction in which the shaft 4c extends. The JT10 axis is spaced apart from the JT11 axis in the direction in which the shaft 4c extends, and is orthogonal to the direction in which the shaft 4c extends and the JT11 axis.

The pair of forceps 4b is attached to the first support 4e so as to rotate about the JT11 axis. The second support 4f supports the first support 4e such that the first support 4e is rotatable about the JT10 axis. That is, the first support 4e is attached to the second support 4f so as to rotate about the JT10 axis. A portion of the first support 4e on the Z1 direction side, which is the tip end side, has a U-shape. TCP1 is set as a tool center point at the center of the tip end of the U-shaped portion of the first support 4e in the JT11 axis.

The pair of forceps 4b as the surgical instrument 4 includes a JT9 axis as a rotation axis of the shaft 4c and a JT12 axis as an opening/closing axis of the pair of forceps 4b. The rotation axis of the shaft 4c is an axis along the direction in which the shaft 4c extends. A plurality of servomotors M2 are provided in the holder 71 of the manipulator arm 60, and rotary bodies of the driven unit 4a are driven by the plurality of servomotors M2. Thus, the surgical instrument 4 is driven around the JT9 axis to the JT12 axis. For example, four servomotors M2 are provided.

Figure 9:
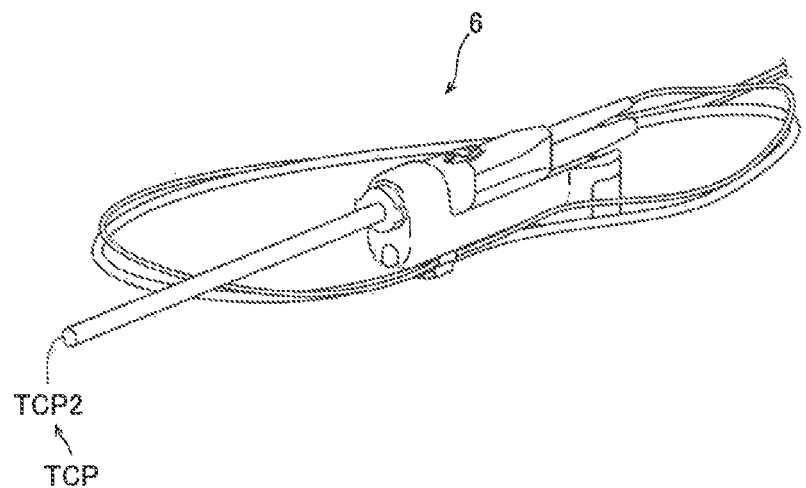
FIG. 9 is a diagram showing an endoscope.

As shown in FIG. 9, TCP2 of the endoscope 6 is set at the tip end of the endoscope 6.

The configuration of the manipulator arms 60 is now described in detail.

As shown in FIG. 6, each of the manipulator arms 60 includes an arm portion 61 and a translation mechanism 70 provided at the tip end of the arm portion 61. The arm portion 61 includes a base 62, links 63, and joints 64. The tip end sides of the manipulator arms 60 three-dimensionally move with respect to the arm base 50 on the base sides of the manipulator arms 60. The arm portion 61 includes a 7-axis articulated robot arm. The plurality of manipulator arms 60 have the same configuration as each other.

Figure 13:
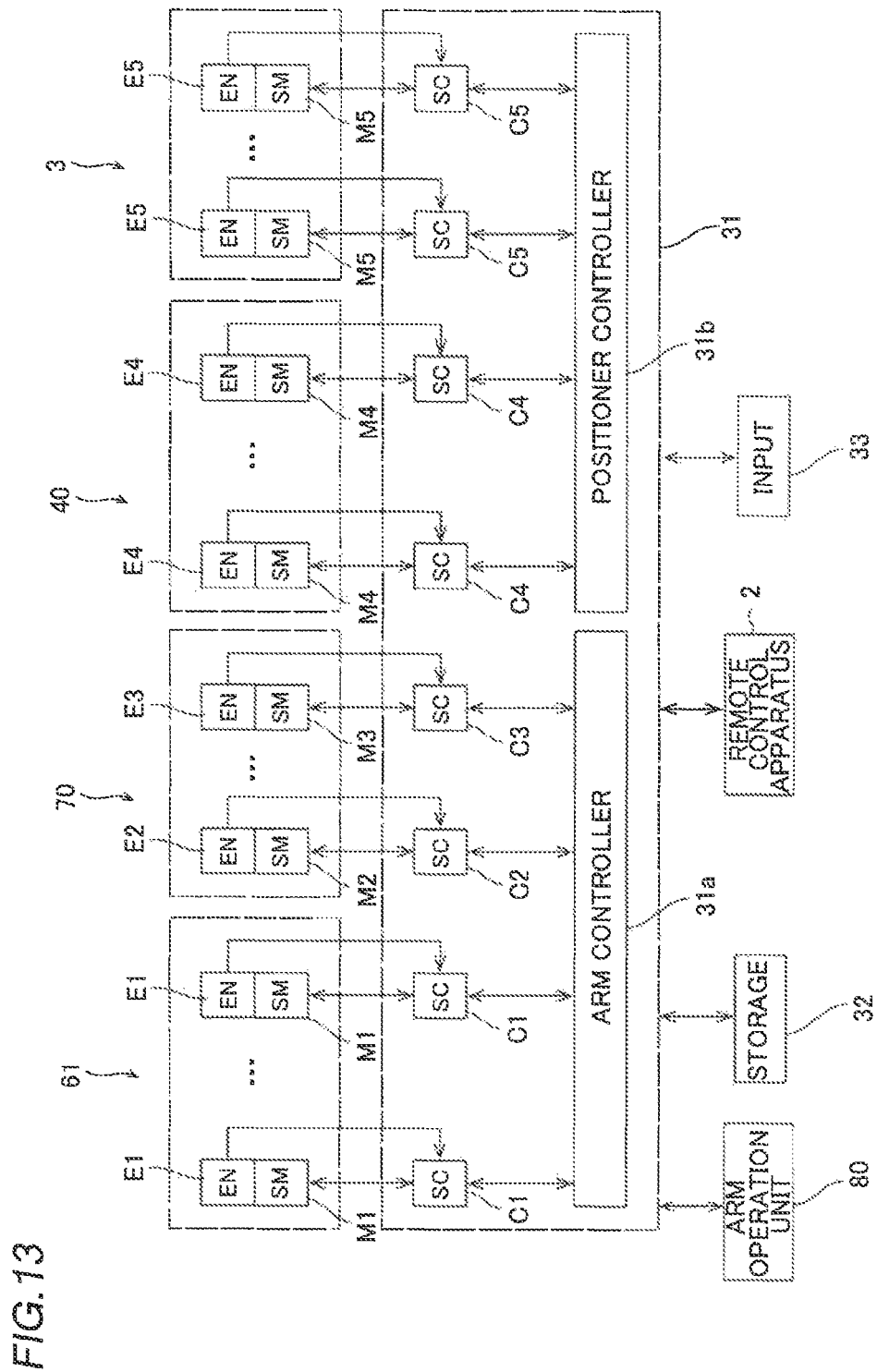
FIG. 13 is a block diagram showing the configuration of a controller of the medical manipulator according to the first embodiment.

As shown in FIG. 6, the manipulator arms 60 each include JT1 to JT7 axes as rotation axes and a JT8 axis as a linear motion axis. The JT1 to JT7 axes correspond to the rotation axes of the joints 64 of the arm portion 61. The JT7 axis corresponds to a base end side link 72 of the translation mechanism 70. The JT8 axis corresponds to an axis that moves a tip end side link 73 of the translation mechanism 70 relative to the base end side link 72 along the Z direction. That is, servomotors M1 shown in FIG. 13 are provided so as to correspond to the JT1 to JT7 axes of the manipulator arm 60. Further, a servomotor M3 is provided so as to correspond to the JT8 axis.

The translation mechanism 70 is provided at the tip end of the arm portion 61, and the surgical instrument 4 is attached thereto. The translation mechanism 70 translates the surgical instrument 4 in a direction in which the surgical instrument 4 is inserted into the patient P. Furthermore, the translation mechanism 70 translates the surgical instrument 4 relative to the arm portion 61. Specifically, the translation mechanism 70 includes the holder 71 that holds the surgical instrument 4. The servomotors M2 shown in FIG. 13 are housed in the holder 71.

Figure 8:
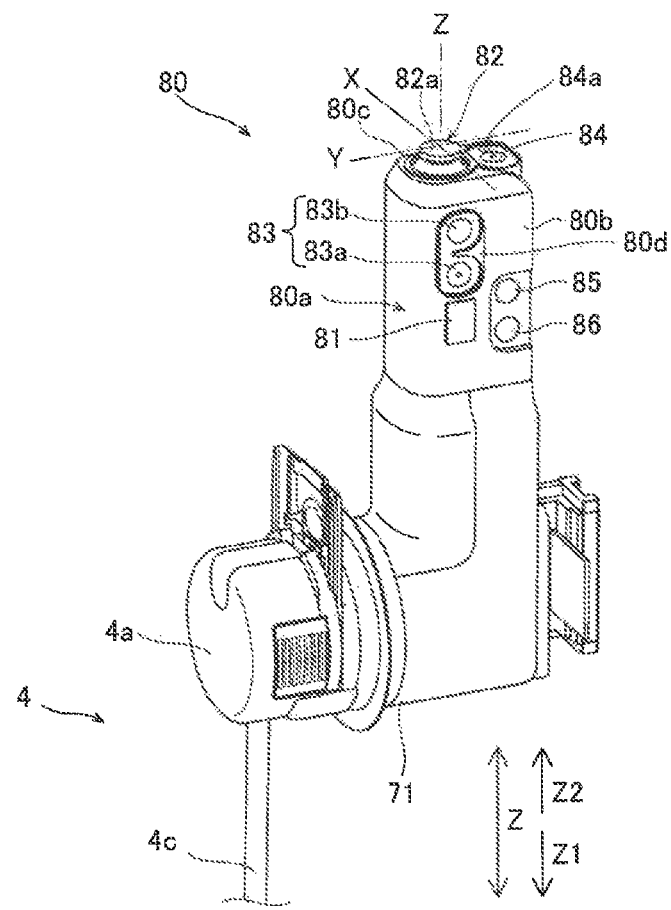
FIG. 8 is a perspective view showing the configuration of an arm operation unit of the medical manipulator according to the first embodiment.

As shown in FIG. 8, the medical manipulator 1 includes an arm operation unit 80 attached to each of the manipulator arms 60 to operate the manipulator arm 60. The arm operation unit 80 includes an enable switch 81, a joystick 82, and a switch unit 83. The enable switch 81 allows or disallows movement of the manipulator arm 60 through the joystick 82 and the switch unit 83. The enable switch 81 gets into a state of allowing movement of the surgical instrument 4 by the manipulator arm 60 when an operator such as a nurse or an assistant grasps the arm operation unit 80 and presses the enable switch 81.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

Figure 10:
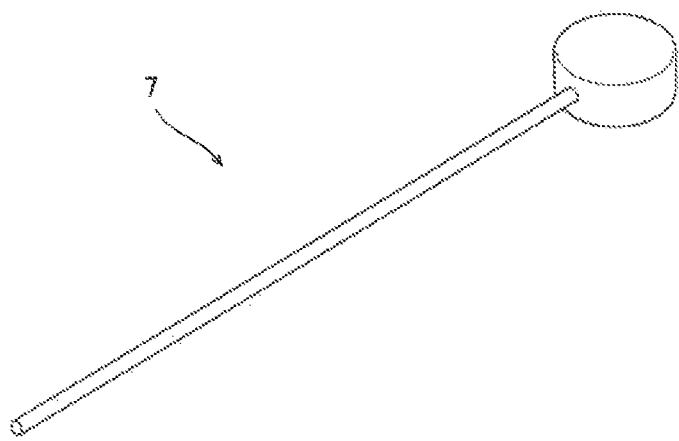
FIG. 10 is a diagram showing a pivot position teaching instrument.
Figure 12:
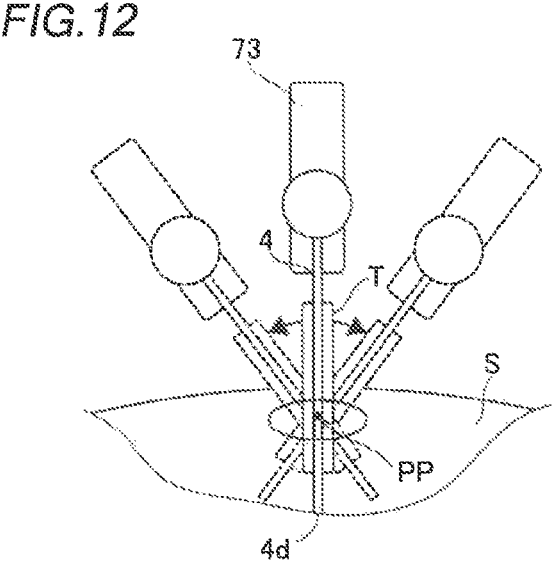
FIG. 12 is a diagram for illustrating rotation of the manipulator arm.

As shown in FIG. 8, the arm operation unit 80 includes a pivot button 85 to teach a pivot position PP that serves as a fulcrum shown in FIG. 12 for movement of the surgical instrument 4 attached to the manipulator arm 60. The pivot button 85 is provided adjacent to the enable switch 81 on a surface 80b of the arm operation unit 80. The pivot button 85 is pressed while the tip end of the endoscope 6 shown in FIG. 9 or a pivot position teaching instrument 7 shown in FIG. 10 is moved to a position corresponding to the insertion position of a trocar T inserted into the body surface S of the patient P such that the pivot position PP is taught and stored in the storage 32. In the teaching of the pivot position PP, the pivot position PP is set as one point, and the direction of the surgical instrument 4 is not set.

As shown in FIG. 1, the endoscope 6 is attached to one (manipulator arm 60c, for example) of the plurality of manipulator arms 60, and surgical instruments 4 other than the endoscope 6 are attached to the remaining manipulator arms 60 (manipulator arms 60a, 60b, and 60d, for example). Specifically, in surgery, the endoscope 6 is attached to one of four manipulator arms 60, and the surgical instruments 4 such as pairs of forceps other than the endoscope 6 are attached to the three manipulator arms 60. The pivot position PP is taught with the endoscope 6 attached to the manipulator arm 60 to which the endoscope 6 is to be attached. Furthermore, pivot positions PP are taught with pivot position teaching instruments 7 attached to the manipulator arms 60 to which the surgical instruments 4 other than the endoscope 6 are to be attached. The endoscope 6 is attached to one of two manipulator arms 60b and 60c arranged in the center among the four manipulator arms 60 arranged adjacent to each other. That is, the pivot position PP is individually set for each of the plurality of manipulator arms 60.

As shown in FIG. 8, an adjustment button 86 for optimizing the position of the manipulator arm 60 is provided on the surface 80b of the arm operation unit 80. After the pivot position PP for the manipulator arm 60 to which the endoscope 6 has been attached is taught, the adjustment button 86 is pressed such that the positions of the other manipulator arms 60 and the arm base 50 are optimized.

Figure 11:
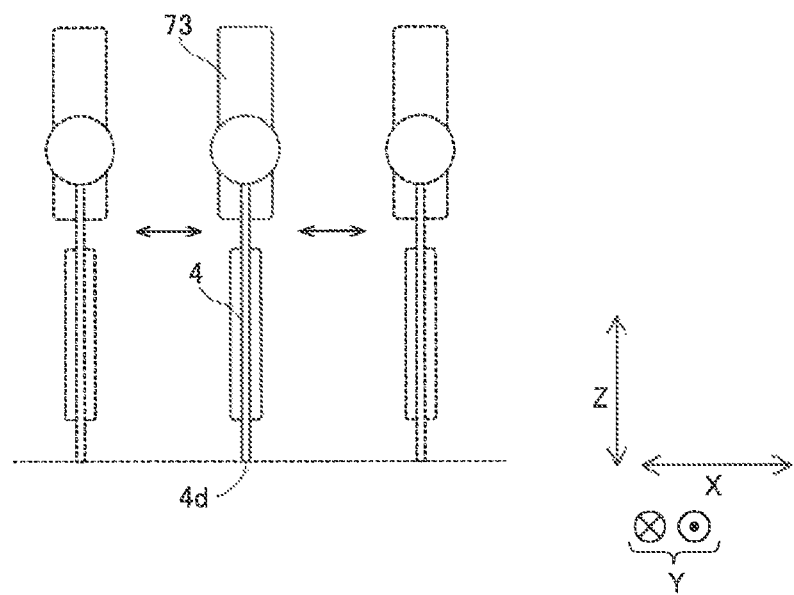
FIG. 11 is a diagram for illustrating translation of the manipulator arm.

As shown in FIG. 8, the arm operation unit 80 includes a mode switching button 84 to switch between a mode for translating the surgical instrument 4 attached to the manipulator arm 60 shown in FIG. 11 and a mode for rotating the surgical instrument 4 shown in FIG. 12. Furthermore, a mode indicator 84a is provided in the vicinity of the mode switching button 84. The mode indicator 84a indicates a switched mode. Specifically, the mode indicator 84a is turned on to indicate a rotation mode or turned off to indicate a translation mode.

The mode indicator 84a also serves as a pivot position indicator that indicates that the pivot position PP has been taught.

As shown in FIG. 11, in the mode for translating the manipulator arm 60, the manipulator arm 60 is moved such that the tip end 4d of the surgical instrument 4 moves on an X-Y plane. As shown in FIG. 12, in the mode for rotating the manipulator arm 60, when the pivot position PP is not taught, the manipulator arm 60 is moved such that the surgical instrument 4 rotates about the pair of forceps 4b, and when the pivot position PP is taught, the manipulator arm 60 is moved such that the surgical instrument 4 rotates about the pivot position PP as a fulcrum. The surgical instrument 4 is rotated while the shaft 4c of the surgical instrument 4 is inserted into the trocar T.

As shown in FIG. 13, the manipulator arm 60 includes a plurality of servomotors M1, encoders E1, and speed reducers so as to correspond to a plurality of joints 64 of the arm portion 61. The encoders E detect the rotation angles of the servomotors M1. The speed reducers slow down rotation of the servomotors M1 to increase the torques.

As shown in FIG. 13, the translation mechanism 70 includes the servomotors M2 to rotate the rotary bodies provided in the driven unit 4a of the surgical instrument 4, the servomotor M3 to translate the surgical instrument 4, encoders E2 and E3, and speed reducers (not shown). The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels of the medical cart 3, respectively, encoders E5, and speed reducers. The encoders E5 detect the rotation angles of the servomotors M5. The speed reducers slow down rotation of the servomotors M5 to increase the torques.

The controller 31 of the medical cart 3 includes an arm controller 31a to control movement of the plurality of manipulator arms 60 based on commands, and a positioner controller 31b to control movement of the positioner 40 and driving of the front wheels of the medical cart 3 based on commands. Servo controllers C1 that controls the servomotors M1 to drive the manipulator arm 60 are electrically connected to the arm controller 31a. The encoders E1 that detect the rotation angles of the servomotors M1 are electrically connected to the servo controllers C1.

Servo controllers C2 that control the servomotors M2 to drive the surgical instrument 4 are electrically connected to the arm controller 31a. The encoders E2 that detect the rotation angles of the servomotors M2 are electrically connected to the servo controllers C2. A servo controller C3 that controls the servomotor M3 to translate the translation mechanism 70 is electrically connected to the arm controller 31a. The encoder E3 that detects the rotation angle of the servomotor M3 is electrically connected to the servo controller C3.

An operation command input to the remote control apparatus 2 is input to the arm controller 31a. The arm controller 31a generates position commands based on the input operation command and the rotation angles detected by the encoders E1 to E3, and outputs the position commands to the servo controllers C1 to C3. The servo controllers C1 to C3 generate torque commands based on the position commands input from the arm controller 31a and the rotation angles detected by the encoders E1 to E3, and output the torque commands to the servomotors M1 to M3. Thus, the manipulator arm 60 is moved according to the operation command input to the remote control apparatus 2.

As shown in FIG. 13, the arm controller 31a of the controller 31 operates the manipulator arm 60 based on an input signal from the joystick 82 of the arm operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the manipulator arm 60 is moved according to the operation command input to the joystick 82.

The arm controller 31a of the controller 31 operates the manipulator arm 60 based on an input signal from the switch unit 83 of the arm operation unit 80. Specifically, the arm controller 31a generates a position command based on an operation command, which is the input signal input from the switch unit 83, and the rotation angle detected by the encoders E1 or the encoder E3, and outputs the position command to the servo controllers C1 or the servo controller C3. The servo controllers C1 or the servo controller C3 generates a torque command based on the position command input from the arm controller 31a and the rotation angle detected by the encoders E1 or the encoder E3, and outputs the torque command to the servomotors M1 or the servomotor M3. Thus, the manipulator arm 60 is moved according to the operation command input to the switch unit 83.

As shown in FIG. 13, servo controllers C4 that control the servomotors M4 to move the positioner 40 are electrically connected to the positioner controller 31b. The encoders E4 that detect the rotation angles of the servomotors M4 are electrically connected to the servo controllers C4. Servo controllers C5 that control the servomotors M5 to drive the front wheels of the medical cart 3 are electrically connected to the positioner controller 31b. The encoders E5 that detect the rotation angles of the servomotors M5 are electrically connected to the servo controllers C5.

An operation command related to setting a preparation position, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 based on an operation command from the input 33.

Figure 14:
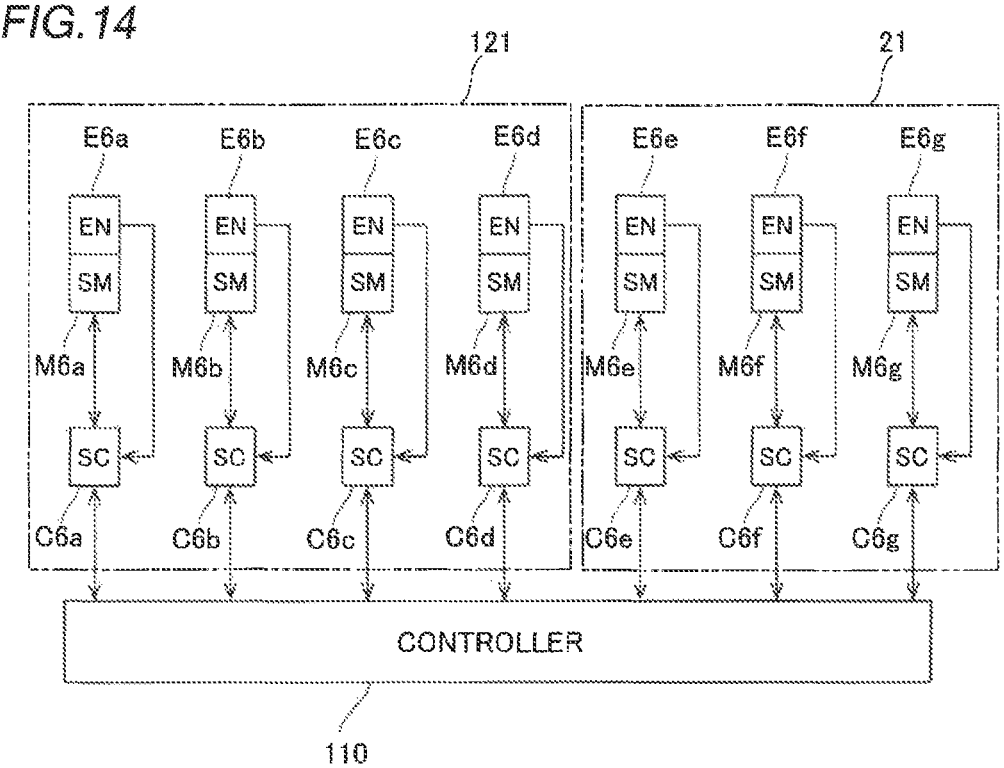
FIG. 14 is a block diagram showing the configuration of a controller of the remote control apparatus according to the first embodiment.

As shown in FIG. 14, the remote control apparatus 2 includes a controller 110. Servo controllers C6a to C6g that control servomotors M6a to M6g provided so as to correspond to the axes A1 to A7, which are the rotation axes of the operation unit 120 including the arms 121 and the operation handle 21, are electrically connected to the controller 110. Furthermore, encoders E6a to E6g that detect the rotation angles of the servomotors M6a to M6g are electrically connected to the servo controllers C6a to C6g. The servomotors M6a to M6g, the servo controllers C6a to C6g, and the encoders E6a to E6g are provided in each of the operation unit 120L and the operation unit 120R. The servomotors M6a to M6g are examples of a drive.

The controller 110 controls the servomotors M6a to M6g to generate torques that cancel gravitational torques generated on the rotation axes A1 to A7 of the servomotors M6a to M6g according to the posture of the operation unit 120. Thus, the operator can operate the operation unit 120 with a relatively small force.

The controller 110 generates torques on the rotation axes A1 to A7 of the servomotors M6a to M6g according to an operation on the operation unit 120, and controls the servomotors M6a to M6g to assist the operation of the operator. Thus, the operator can operate the operation unit 120 with a relatively small force.

Figure 15:
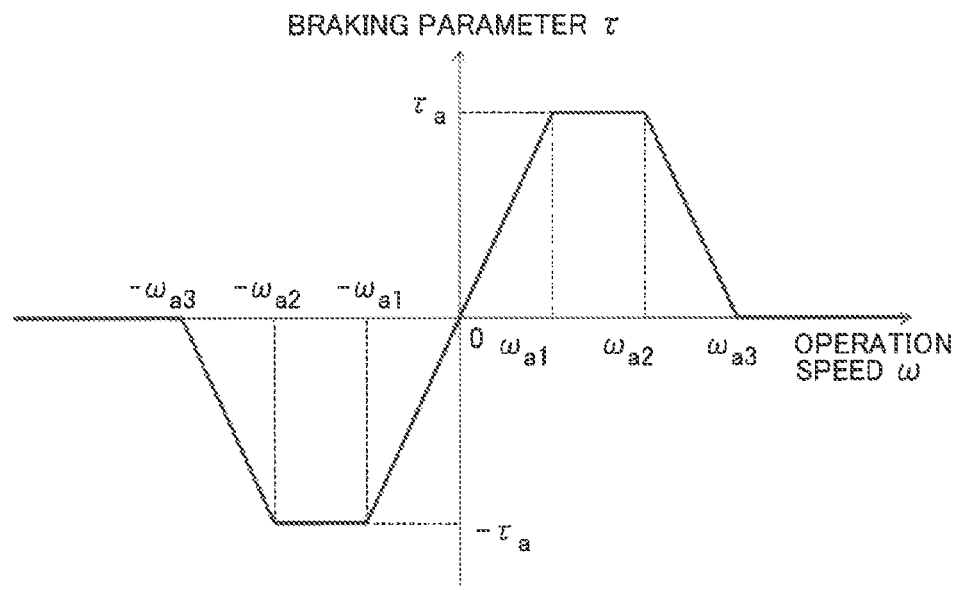
FIG. 15 is a diagram showing a braking parameter during acceleration according to the first embodiment.

In the first embodiment, the controller 110 controls the servomotors to exert a braking force when an operation on the operation unit 120 is decelerated and/or accelerated. Specifically, as shown in FIG. 15, the controller 110 controls the servomotors to exert a braking force when the operation on the operation unit 120 is accelerated. That is, the controller 110 exerts a braking force by software during acceleration. Furthermore, the controller 110 performs a control to increase the braking force with respect to at least one of the plurality of servomotors when the operation on the operation unit 120 is decelerated and/or accelerated. Specifically, the controller 110 performs a control to exert a braking force on servomotors corresponding to rotation axes involved in moving the surgical instrument 4 by the manipulator arm 60 when the operation on the operation unit 120 is decelerated and/or accelerated. More specifically, the controller 110 performs a control to exert a braking force on the servomotors M6a, M6b, and M6c corresponding to the A1, A2, and A3 axes. The servomotors M6a, M6b, and M6c correspond to operations for moving the manipulator arm 60 three-dimensionally. The controller 110 may be applied to an axis other than the A1, A2, and A3 axes. For example, the controller 110 performs a control to exert a braking force on M6g corresponding to the A7 axis. The servomotor M6g corresponds to an operation for rotating the pair of forceps 4b about an axis along the shaft 4c.

Figure 17:
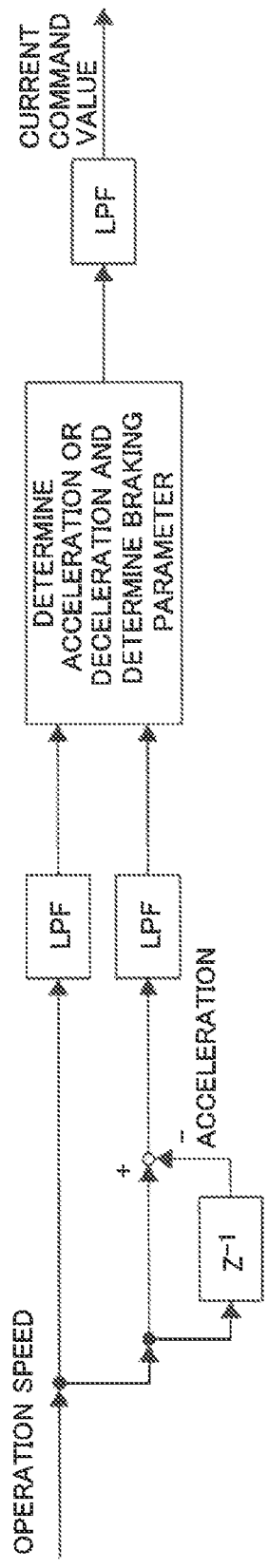
FIG. 17 is a control block diagram of the controller of the remote control apparatus according to the first embodiment.

Specifically, as shown in FIG. 17, the operation speed $\omega$ of the operation unit 120 is input to the controller 110. The operation speed $\omega$ refers to a rotation speed at which the operation unit 120 is rotated about the A1, A2, or A3 axis. The controller 110 applies a low-pass filter, which is shown as LPF in FIG. 17, to the input operation speed $\omega$. Furthermore, the controller 110 calculates acceleration from a difference in the input rotation speed and applies a low-pass filter to the calculated acceleration. Then, the controller 110 determines whether the operation unit 120 is accelerated or decelerated based on the operation speed $\omega$ and the calculated acceleration. Furthermore, the controller 110 determines braking parameters $\tau$ based on the determination of acceleration or deceleration. Then, the controller 110 applies a low-pass filter to current command values corresponding to the determined braking parameters $\tau$, and then outputs the current command values to the servo controllers C6a, C6b, and C6c. Thus, a braking force acts on the servomotors M6a, M6b, and M6c.

In the first embodiment, the controller 110 determines the braking parameters $\tau$ of the servomotors M6a, M6b, and M6c according to the operation speed at which the operation unit 120 is operated, and controls the servomotors M6a, M6b, and M6c to exert a braking force using the determined braking parameters $\tau$. In the following description, rotation to a first side about each of the axes of A1, A2, and A3 is defined as rotation in a positive direction, and rotation to a second side is defined as rotation in a negative direction.

In the first embodiment, as shown in FIG. 15, when the operation is accelerated, the controller 110 increases the absolute value of the braking parameter $\tau$ as the absolute value of the operation speed $\omega$ increases when the absolute value of the operation speed $\omega$ is less than a fifth threshold, maintains the braking parameter $\Xi$ constant when the absolute value of the operation speed $\omega$ is equal to or greater than the fifth threshold and is less than a sixth threshold, decreases the absolute value of the braking parameter $\tau$ as the absolute value of the operation speed $\omega$ increases when the absolute value of the operation speed $\omega$ is equal to or greater than the sixth threshold and is less than a seventh threshold, and sets the braking parameter $\tau$ to zero when the absolute value of the operation speed $\omega$ is equal to or greater than the seventh threshold. Specifically, when the operation is accelerated, the controller 110 increases the braking parameter $\tau$ as the operation speed $\omega$ increases when the operation speed $\omega$ is less than a threshold $\omega_{a1}$, sets the braking parameter $\tau$ to constant $\tau_a$ when the operation speed $\omega$ is equal to or greater than the threshold $\omega_{a1}$ and is less than a threshold $\omega_{a2}$, decreases the braking parameter $\tau$ as the operation speed $\omega$ increases when the operation speed $\omega$ is equal to or greater than the threshold $\omega_{a2}$ and is less than a threshold $\omega_{a3}$, and sets the braking parameter $\tau$ to zero when the operation speed $\omega$ is equal to or greater than the threshold $\omega_{a3}$. When the operation is accelerated, the controller 110 increases the braking parameter $\tau$ as the operation speed $\omega$ increases when the operation speed $\omega$ is greater than a threshold $-\omega_{a1}$, sets the braking parameter $\tau$ to constant $-\tau_a$ when the operation speed $\omega$ is equal to or greater than a threshold $-\omega_{a2}$ and is less than the threshold $-\omega_{a1}$, decreases the braking parameter $\tau$ as the operation speed $\omega$ increases when the operation speed $\omega$ is equal to or greater than a threshold $-\omega_{a3}$ and is less than the threshold $-\omega_{a2}$, and sets the braking parameter $\tau$ to zero when the operation speed c$\omega$ is equal to or less than the threshold $-\omega_{a3}$. The threshold $\omega_{a1}$ and the threshold $-\omega_{a1}$ are examples of a fifth threshold. The threshold $\omega_{a2}$ and the threshold $-\omega_{a2}$ are examples of a sixth threshold. The threshold $\omega_{a3}$ and the threshold $-\omega_{a3}$ are examples of a seventh threshold.

The negative operation speed $\omega$ indicates that the servomotor rotates in a reverse direction.

When the operation speed $\omega$ is between the threshold $\omega_{a1}$ and the threshold $\omega_{a1}$, the braking parameter $\tau$ increases linearly. When the operation speed $\omega$ is between the threshold $\omega_{a2}$ and the threshold $\omega_{a3}$, the braking parameter $\tau$ decreases linearly. When the operation speed $\omega$ is between the threshold $-\omega_{a2}$ and the threshold $-\omega_{a3}$, the braking parameter $\tau$ increases linearly. When the operation speed $\omega$ is 0, the braking parameter $\tau$ is 0.

Figure 16:
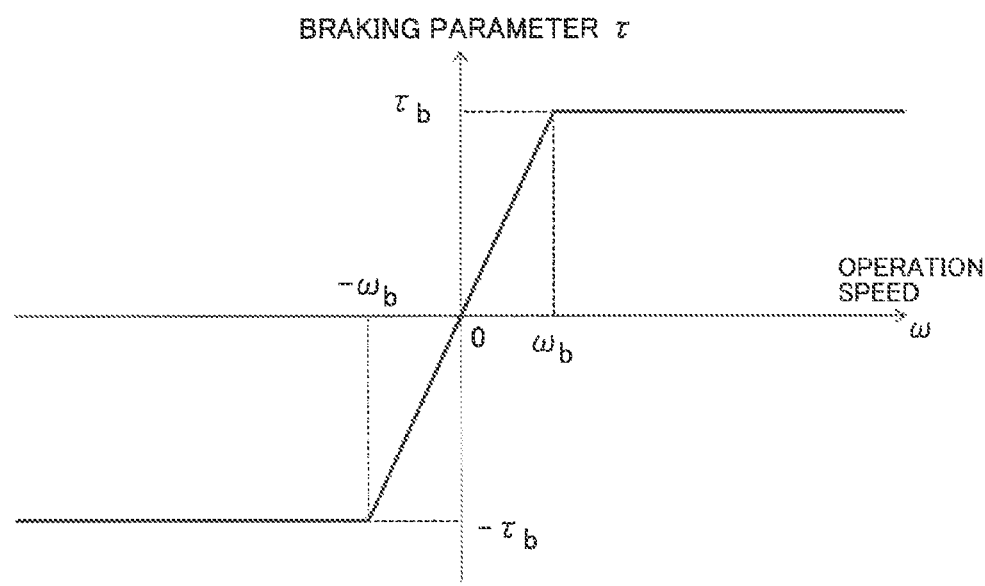
FIG. 16 is a diagram showing a braking parameter during deceleration according to the first embodiment.

In the first embodiment, as shown in FIG. 16, the controller 110 controls the servomotors to exert a braking force when the operation on the operation unit 120 is decelerated. That is, the controller 110 exerts a braking force by software during deceleration. Specifically, when the operation is decelerated, the controller 110 maintains the braking parameter $\tau$ constant when the absolute value of the operation speed $\omega$ is greater than a first threshold, and decreases the absolute value of the braking parameter $\tau$ as the absolute value of the operation speed $\omega$ decreases when the absolute value of the operation speed $\omega$ is equal to or less than the first threshold. More specifically, when the operation is decelerated, the controller 110 sets the braking parameter $\tau$ to constant $\tau_b$ when the operation speed $\omega$ is greater than a threshold $\omega_b$, and decreases the braking parameter $\tau$ as the operation speed $\omega$ decreases when the operation speed $\omega$ is equal to or less than the threshold $\omega_b$. When the operation is decelerated, the controller 110 maintains the braking parameter $\tau$ constant when the operation speed $\omega$ is less than a threshold $-\omega_b$, and increases the braking parameter $\tau$ as the operation speed $\omega$ increases when the operation speed $\omega$ is equal to or greater than the threshold $-\omega_b$. The threshold $\omega_b$ and the threshold $-\omega_b$ are examples of a first threshold.

Specifically, when the operation speed $\omega$ is between the threshold $\omega_b$ and 0, the braking parameter $\tau$ decreases linearly. When the operation speed $\omega$ is between the threshold $-\omega_b$ and 0, the braking parameter $\tau$ increases linearly. When the operation speed $\omega$ is 0, the braking parameter $\tau$ is 0.

Figure 18:
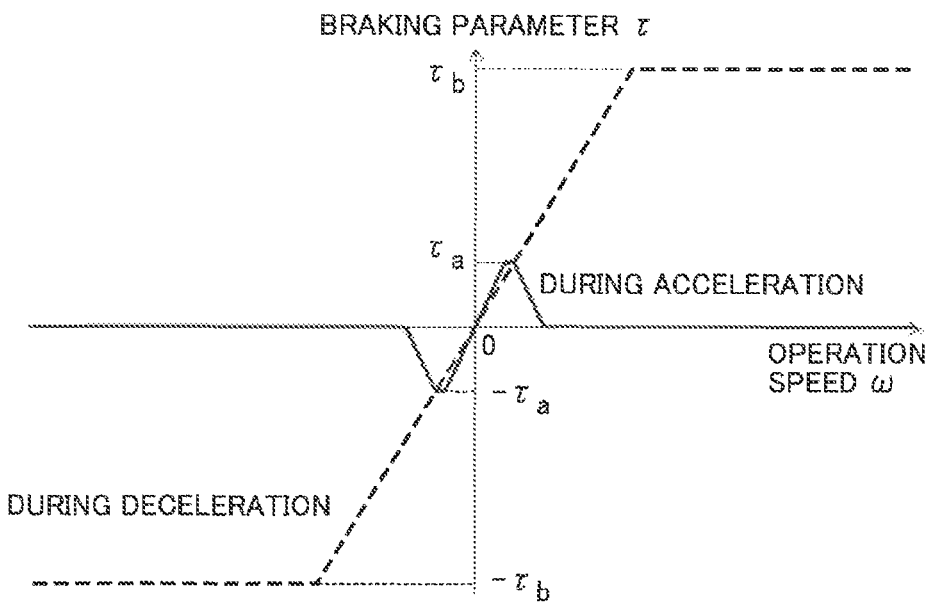
FIG. 18 is a diagram showing a braking parameter during acceleration and deceleration according to the first embodiment.

In the first embodiment, the controller 110 increases the maximum of the absolute value of the braking parameter $\tau_b$ during deceleration of the operation to greater than the maximum of the absolute value of the braking parameter $\tau_a$ during acceleration of the operation. For example, in the first embodiment, as shown in FIG. 18, the maximum of the braking parameter $\tau_b$ during deceleration of the operation shown by a dotted line is four times the maximum of the braking parameter $\tau_a$ during acceleration of the operation shown by a solid line.

In the first embodiment, as shown in FIG. 1, a storage 111 is provided to store the braking parameters $\tau$. The storage 111 is provided in the remote control apparatus 2, for example. The controller 110 determines the braking parameter $\tau$ based on a table in which the operation speed $\omega$ and the braking parameter $\tau$ are associated with each other. That is, the relationship between the operation speed $\omega$ and the braking parameter $\tau$ shown in FIGS. 15 and 16 is stored in the table form in the storage 111.

Figure 19:
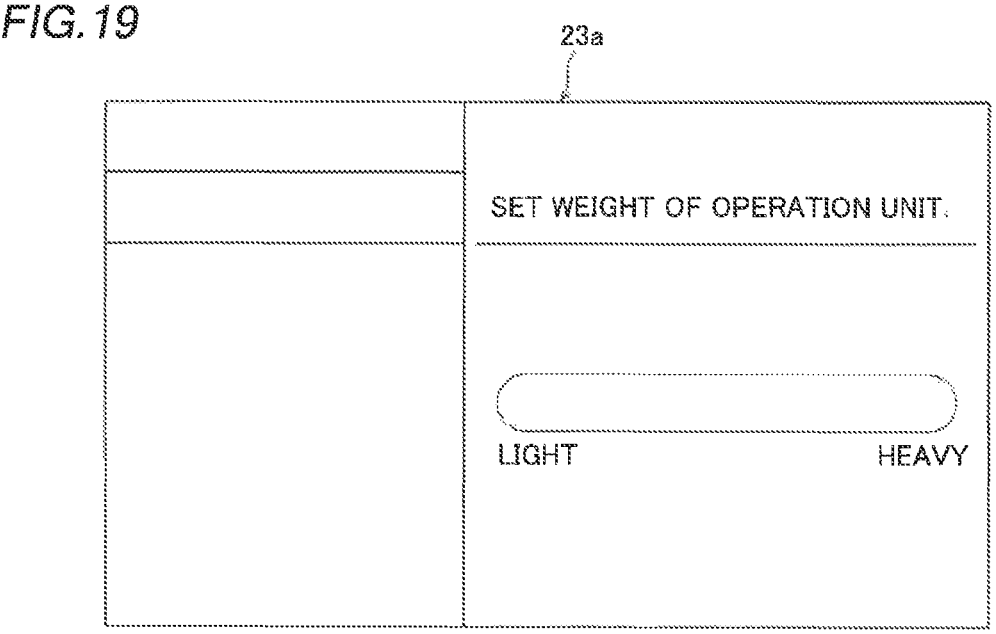
FIG. 19 is a diagram showing a braking parameter selector according to the first embodiment.

In the first embodiment, as shown in FIG. 19, a braking parameter selector 23a is provided to receive a selection of the magnitude of the braking parameter $\tau$. The braking parameter selector 23a is provided in the remote control apparatus 2. Specifically, the braking parameter selector 23a includes the touch panel 23 of the remote control apparatus 2.

Figure 20:
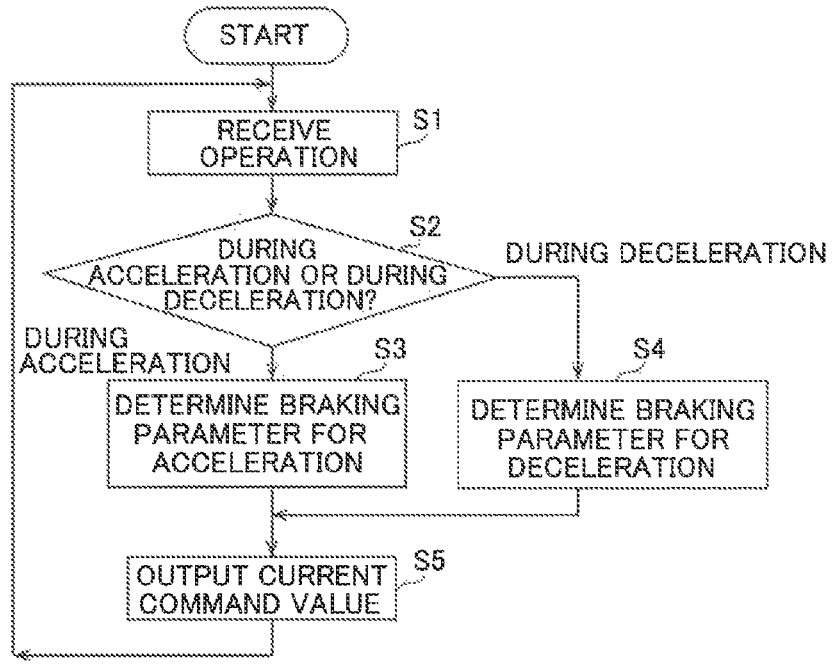
FIG. 20 is a diagram showing a control flow of the remote control apparatus according to the first embodiment.

A control flow of the surgical system 100 is now described with reference to FIG. 20.

In step S1, an operation on the operation unit 120 is received. Thus, an operation speed $\omega$ corresponding to the received operation is input to the controller 110.

In step S2, the controller 110 calculates acceleration from the input operation speed $\omega$. Then, the controller 110 determines whether the current operation corresponds to acceleration or deceleration based on the input operation speed $\omega$ and the calculated acceleration. Specifically, when the operation speed $\omega$ is positive and the acceleration is positive, it is determined that the current operation is being accelerated. When the operation speed $\omega$ is positive and the acceleration is 0, it is determined that the current operation is being accelerated. The acceleration of 0 indicates a constant speed. When the operation speed $\omega$ is positive and the acceleration is negative, it is determined that the current operation is being decelerated. When the operation speed $\omega$ is 0 and the acceleration is positive, it is determined that the current operation is being accelerated. When the operation speed $\omega$ is 0 and the acceleration is 0, it is determined that the current operation is being accelerated. When the operation speed $\omega$ is 0 and the acceleration is negative, it is determined that the current operation is being decelerated. When the operation speed $\omega$ is negative and the acceleration is positive, it is determined that the current operation is being decelerated. When the operation speed $\omega$ is negative and the acceleration is 0, it is determined that the current operation is being decelerated. When the operation speed $\omega$ is negative and the acceleration is negative, it is determined that the current operation is being accelerated.

When it is determined in step S2 that the current operation is being accelerated, the process advances to step S3. In step S3, the braking parameter $\tau$ for acceleration shown in FIG. 15 is determined according to the input operation speed $\omega$. Then, the process advances to step S5.

When it is determined in step S2 that the current operation is being decelerated, the process advances to step S4. In step S4, the braking parameter $\tau$ for deceleration shown in FIG. 16 is determined according to the input operation speed $\omega$. Then, the process advances to step S5.

In step S5, the controller 110 outputs current command values for the servomotors M6a, M6b, and M6c to the servo controllers C6a, C6b, and C6c such that a braking force is exerted using the determined braking parameter $\tau$. The operations in step S2 to step S5 described above are performed in each control cycle of the controller 110, for example.

A braking force acting when the operator tries to stop the operation unit 120 is now described.

First, when the operator tries to stop the operation unit 120, the operation speed $\omega$ is decreased. In this case, a braking force during deceleration acts on the operation unit 120. When the operation speed $\omega$ becomes equal to or less than the threshold $\omega_b$, the braking force decreases as the operation speed $\omega$ decreases. Then, the operation unit 120 is stopped. In this manner, the braking force acts during deceleration, and thus overshoot caused by the inertia of the operation unit 120 when the operator tries to stop the operation unit 120 suddenly is significantly reduced or prevented.

Even when the operator tries to make their hand operating the operation unit 120 stationary, their hand may move unintentionally. For example, their hand may move unintentionally due to spasms of the operator's hand muscles or the operator's breathing. When the operation unit 120 advances further than a position at which the operator tries to stop the operation unit 120 due to inertia, the operator may unintentionally try to return the operation unit 120 to a desired position. In such a case, the operation unit 120 is in an accelerated state. During acceleration, a braking force acts so as to increase as the operation speed $\omega$ increases such that it is possible to significantly reduce or prevent unintentional movement of the operation unit 120 described above.

Advantages of First Embodiment

According to the first embodiment, the following advantages are achieved.

According to the first embodiment, as described above, the controller 110 is configured or programmed to control the servomotors M6a, M6b, and M6c to exert a braking force when an operation on the operation unit 120 is decelerated and/or accelerated. Accordingly, the braking force is exerted during deceleration such that overshoot caused by the inertia of the operation unit 120 when the operator tries to stop the operation unit 120 suddenly is significantly reduced or prevented. Furthermore, the braking force is exerted during acceleration such that movement of the operation unit 120 due to a reaction caused when the operation unit 120 is suddenly stopped, for example, is significantly reduced or prevented. Thus, the operation unit 120 of the remote control apparatus 2 can be stopped at an appropriate position.

According to the first embodiment, as described above, the controller 110 is configured or programmed to determine the braking parameters $\tau$ of the servomotors M6a, M6b, and M6c according to the operation speed at which the operation unit 120 is operated, and to control the servomotors M6a, M6b, and M6c to exert a braking force using the determined braking parameter $\tau$. Accordingly, the braking parameter $\tau$ is adjusted such that the braking force can be appropriately exerted.

According to the first embodiment, as described above, the controller 110 is configured or programmed to, when the operation is decelerated, maintain the braking parameter τ constant when the operation speed ω is greater than the threshold $ω_b$, and decrease the braking parameter τ as the operation speed ω decreases when the operation speed ω is equal to or less than the threshold $ω_b$. Furthermore, the controller 110 is configured or programmed to, when the operation is decelerated, maintain the braking parameter τ constant when the operation speed ω is less than the threshold $-ω_b$, and increase the braking parameter τ as the operation speed ω increases when the operation speed ω is equal to or greater than the threshold $-ω_b$. Accordingly, when the operation speed ω is near zero, it is possible to significantly reduce a sense of discomfort in operation due to switching between positive and negative braking parameters τ when the operation speed ω is near zero.

According to the first embodiment, as described above, the controller 110 is configured or programmed to, when the operation is accelerated, increase the braking parameter τ as the operation speed ω increases when the operation speed ω is equal to or less than the threshold $ω_{a1}$, and increase the braking parameter τ as the operation speed ω increases when the operation speed ω is equal to or greater than the threshold $-ω_{a1}$. Accordingly, it is possible to significantly reduce a sense of discomfort in operation due to switching between positive and negative braking parameters τ when the operation speed ω is near zero. Furthermore, when the operation speed ω is equal to or greater than the threshold $ω_{a3}$ or equal to or less than the threshold $-ω_{a3}$, the braking force becomes zero, and thus the operation at high speed can be lightened.

According to the first embodiment, as described above, the controller 110 is configured or programmed to increase the maximum of the absolute value of the braking parameter τ during deceleration of the operation to greater than the maximum of the absolute value of the braking parameter τ during acceleration of the operation. Accordingly, the braking force becomes relatively large during deceleration, and thus the operation unit 120 can be stopped more quickly.

According to the first embodiment, as described above, the controller 110 is configured or programmed to determine the braking parameter τ based on the table stored in the storage 111 in which the operation speed ω and the braking parameter τ are associated with each other. Accordingly, the controller 110 can easily determine the braking parameter τ by referring to the table stored in the storage 111.

According to the first embodiment, as described above, the surgical system 100 includes the braking parameter selector 23a to receive a selection of the magnitude of the braking parameter τ. Accordingly, the magnitude of the braking force can be adjusted according to the preference of the operator.

According to the first embodiment, as described above, the braking parameter selector 23a is provided in the remote control apparatus 2. Accordingly, the braking parameter selector 23a is arranged in the vicinity of the operator who operates the remote control apparatus 2, and thus the operator can easily operate the braking parameter selector 23a.

According to the first embodiment, as described above, the controller 110 is configured or programmed to perform a control to increase a braking force with respect to the servomotors M6a, M6b, and M6c when the operation on the operation unit 120 is decelerated and/or accelerated. Accordingly, when the surgical instrument 4 is moved by the manipulator arm 60, the operation unit 120 of the remote control apparatus 2 can be stopped at an appropriate position.

Second Embodiment

A braking parameter τ according to a second embodiment is now described with reference to FIGS. 21 and 22.

Figure 21:
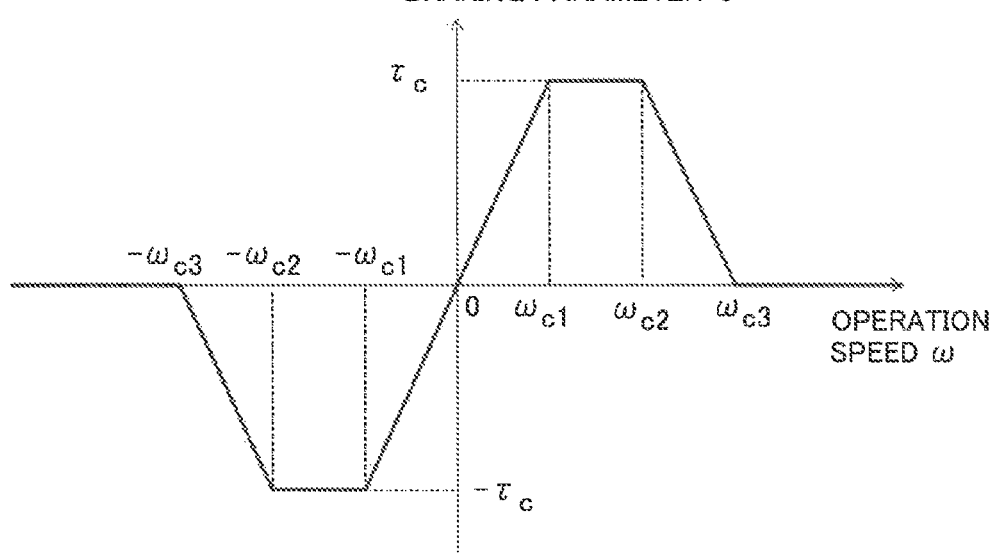
FIG. 21 is a diagram showing a braking parameter during deceleration according to a second embodiment.
Figure 22:
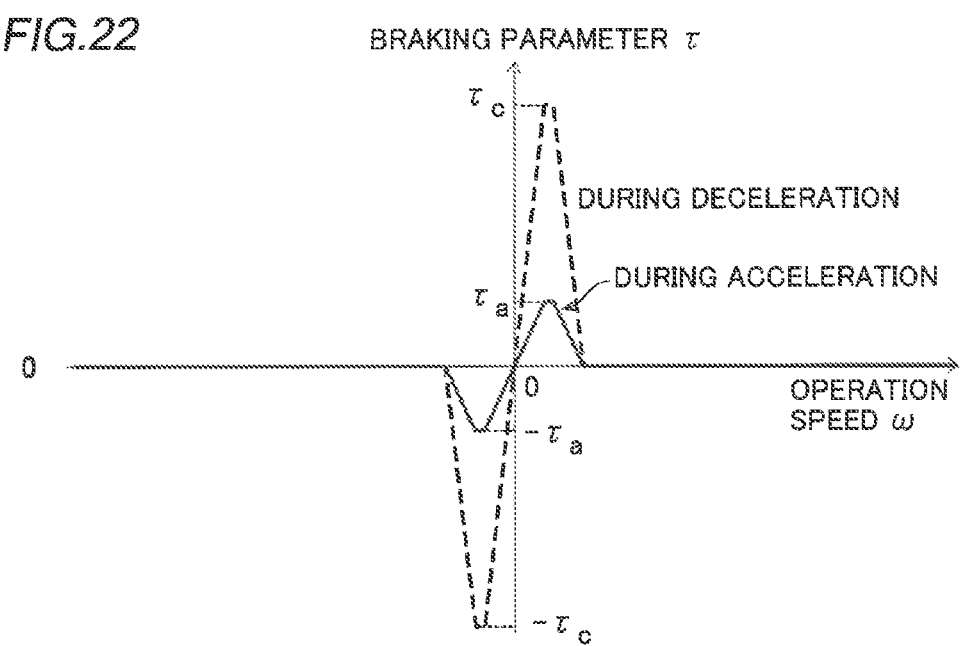
FIG. 22 is a diagram showing a braking parameter during acceleration and deceleration according to the second embodiment.

In the second embodiment, as shown in FIGS. 21 and 22, when an operation is decelerated, the controller 110 sets the braking parameter τ to zero when the absolute value of an operation speed ω is greater than a second threshold, increases the absolute value of the braking parameter τ as the absolute value of the operation speed ω decreases when the absolute value of the operation speed ω is equal to or less than the second threshold and is greater than a third threshold, maintains the braking parameter τ constant when the absolute value of the operation speed ω is equal to or less than the third threshold and is greater than a fourth threshold, and decreases the absolute value of the braking parameter τ as the absolute value of the operation speed ω decreases when the absolute value of the operation speed ω is equal to or less than the fourth threshold. Specifically, the controller 110 sets the braking parameter τ to zero when the operation speed ω is greater than a threshold $Ω_{c3}$ during deceleration of the operation, increases the braking parameter τ as the operation speed ω decreases when the operation speed ω is equal to or less than the threshold $ω_{c3}$ and is greater than a threshold $ω_{c2}$, sets the braking parameter τ to constant $τ_c$ when the operation speed ω is equal to or less than the threshold $ω_{c2}$ and is greater than a threshold $ω_{c1}$, and decreases the braking parameter τ as the operation speed ω decreases when the operation speed ω is equal to or less than the threshold $ω_{c1}$. Furthermore, the controller 110 sets the braking parameter τ to zero when the operation speed ω is less than a threshold $-ω_{c3}$ during deceleration of the operation, decreases the braking parameter τ as the operation speed ω increases when the operation speed ω is equal to or greater than the threshold $-ω_{c3}$ and is less than a threshold $-ω_{c2}$, sets the braking parameter τ to constant $τ_c$ when the operation speed ω is equal to or greater than the threshold $-ω_{c2}$ and is less than a threshold $-ω_{c1}$, and increases the braking parameter τ as the operation speed ω increases when the operation speed ω is equal to or greater than the threshold $-ω_{c1}$. The threshold $ω_{c1}$ and the threshold $-ω_{c1}$ are examples of a fourth threshold. The threshold $ω_{c2}$ and the threshold $-ω_{c2}$ are examples of a third threshold. The threshold $ω_{c3}$ and the threshold $-ω_{c3}$ are examples of a second threshold.

When the operation speed ω is between the threshold value $ω_{c3}$ and the threshold $ω_{c2}$ and between the threshold $-ω_{c3}$ and the threshold $-ω_{c2}$, the absolute value of the braking parameter τ increases linearly. When the operation speed ω is between the threshold $ω_{c1}$ and 0 and between the threshold $-ω_{c1}$ and 0, the absolute value of the braking parameter τ decreases linearly. When the operation speed ω is 0, the braking parameter τ is 0. The braking parameter τ during acceleration according to the second embodiment is similar to the braking parameter τ according to the first embodiment shown in FIG. 15. That is, in the second embodiment, the braking parameter τ during acceleration and the braking parameter τ during deceleration change in the same manner. As shown in FIG. 22, the maximum of the absolute value of the braking parameter $τ_c$ during deceleration is four times or more than the maximum of the absolute value of the braking parameter $τ_a$ during acceleration.

For example, as shown in FIG. 18, when the braking parameter τ during deceleration is a relatively large constant value $τ_b$ as in the first embodiment at high speed, and the braking parameter τ during acceleration is 0 as in the first embodiment at high speed, there may be a sense of discomfort in operation of an operation unit 120 due to a large difference between the braking parameter $\tau_b$ during deceleration and the braking parameter of 0 during acceleration when the accelerated state and the decelerated state of the operation on the operation unit 120 are switched. Therefore, in the second embodiment, as shown in FIG. 21, the braking parameter $\tau$ during deceleration is set to 0 at high speed so as to be similar to the braking parameter $\tau$ during acceleration such that a sense of discomfort in operation can be significantly reduced when the accelerated state and the decelerated state are switched.

Advantages of Second Embodiment

According to the second embodiment, the following advantages are achieved.

According to the second embodiment, as described above, when an operation on the operation unit 120 is decelerated, the difference between the braking parameter $\tau$ during deceleration and the braking parameter $\tau$ during acceleration is decreased. Accordingly, a sense of discomfort in operation can be reduced. Furthermore, when the operation speed $\omega$ is equal to or less than the threshold $\omega_{c1}$, the braking parameter $\tau$ is decreased as the operation speed $\omega$ decreases, and when the operation speed $\omega$ is equal to or greater than the threshold $-\omega_{c1}$, the braking parameter $\tau$ is increased as the operation speed $\omega$ increases. Thus, it is possible to significantly reduce a sense of discomfort in operation due to switching between positive and negative braking parameters when the operation speed $\omega$ is near zero.

Modified Examples

The embodiments disclosed this time must be considered as illustrative in all points and not restrictive. The scope of the present disclosure is not shown by the above description of the embodiments but by the scope of claims for patent, and all modifications (modified examples) within the meaning and scope equivalent to the scope of claims for patent are further included.

For example, while when an operation is accelerated, the braking parameter $\tau$ is set to zero when the operation speed $\omega$ is greater than the threshold $\omega_{a3}$ or less than the threshold $-\omega_{a3}$ in the aforementioned first embodiment, the present disclosure is not limited to this. For example, the braking parameter $\tau$ may alternatively be set to a value other than 0 when the operation speed $\omega$ is greater than the threshold $\omega_{a3}$ or less than the threshold $-\omega_{a3}$.

While the braking parameter $\tau$ becomes constant when the operation speed $\omega$ is between the threshold $\omega_{a1}$ and the threshold $\omega_{a2}$ and between the threshold $-\omega_{a1}$ and the threshold $-\omega_{a2}$ in the aforementioned first embodiment, the present disclosure is not limited to this. For example, the braking parameter $\tau$ may alternatively be decreased when the operation speed $\omega$ becomes greater than the threshold $\omega_{a1}$, and the braking parameter $\tau$ may alternatively be increased when the operation speed $\omega$ becomes less than the threshold $-\omega_{a1}$.

While the braking parameter $\tau$ becomes constant when the operation speed $\omega$ is between the threshold $\omega_{c1}$ and the threshold $\omega_{c2}$ and between the threshold $-\omega_{c1}$ and the threshold $-\omega_{c2}$ in the aforementioned second embodiment, the present disclosure is not limited to this. For example, the braking parameter $\tau$ may alternatively be decreased when the operation speed $\omega$ becomes greater than the threshold $\omega_{c1}$, and the braking parameter $\tau$ may alternatively be increased when the operation speed $\omega$ becomes less than the threshold $-\omega_{c1}$.

While the maximum of the absolute value of the braking parameter $\tau$ during deceleration of the operation is increased to greater than the maximum of the absolute value of the braking parameter $\tau$ during acceleration of the operation in each of the aforementioned first and second embodiments, the present disclosure is not limited to this. For example, the maximum of the absolute value of the braking parameter $\tau$ during deceleration of the operation may alternatively be the same as the maximum of the absolute value of the braking parameter $\tau$ during accelerating of the operation.

While the braking parameter selector 23a is provided in the remote control apparatus 2 in each of the aforementioned first and second embodiments, the present disclosure is not limited to this. For example, the braking parameter selector 23a may alternatively be provided in an apparatus other than the remote control apparatus 2.

While the controller 110 of the remote control apparatus 2 performs a control to exert a braking force in each of the aforementioned first and second embodiments, the present disclosure is not limited to this. For example, a controller other than the controller 110 of the remote control apparatus 2 may alternatively perform a control to exert a braking force.

Figure 23:
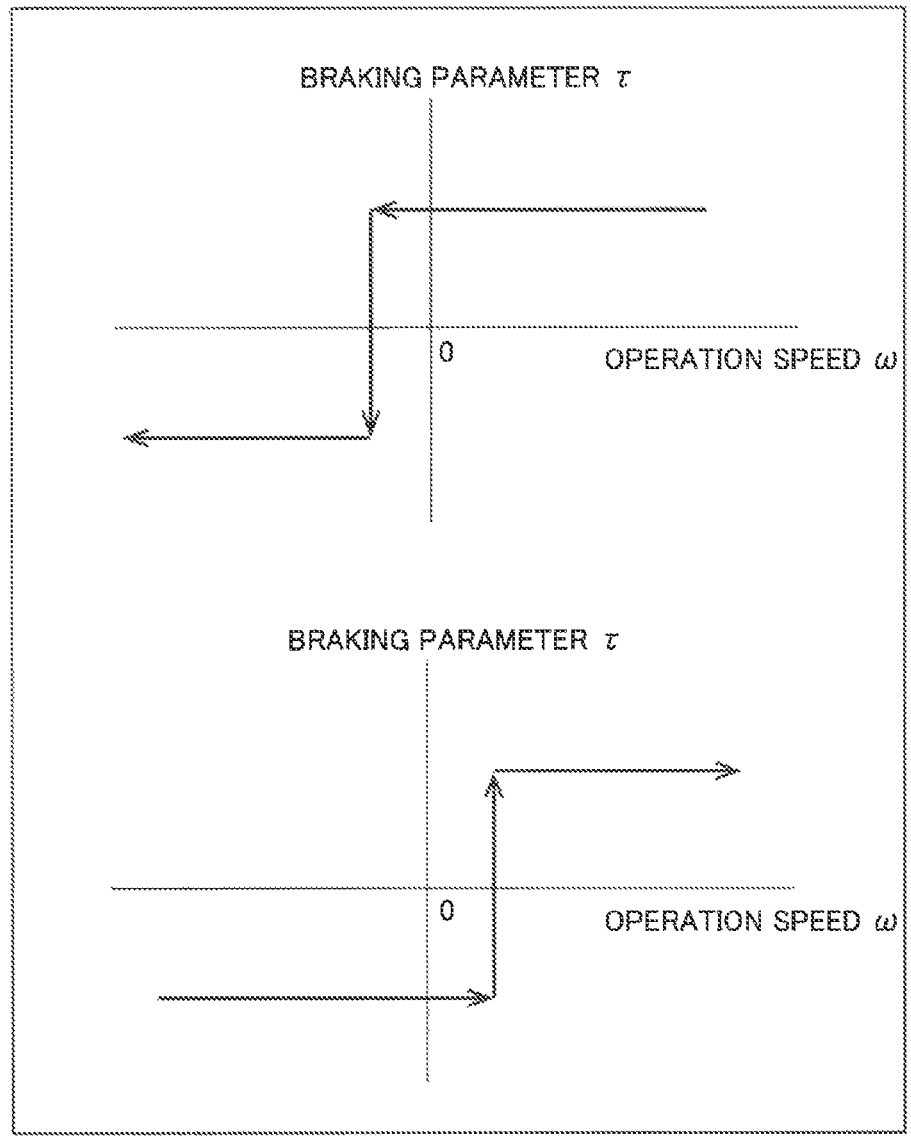
FIG. 23 is a diagram for illustrating a braking parameter during acceleration and deceleration according to a modified example.

While a change in the braking parameter $\tau$ is the same when the operation speed $\omega$ decreases and when the operation speed $\omega$ increases in each of the aforementioned first and second embodiments, the present disclosure is not limited to this. For example, the hysteresis as shown in FIG. 23 may alternatively be applied to the braking parameters $\tau$ according to the first and second embodiments. That is, the change in the braking parameter $\tau$ may be different when the operation speed $\omega$ changes from the positive side to the negative side and when the operation speed $\omega$ changes from the negative side to the positive side, and the braking parameter $\tau$ may not be changed near the operation speed $\omega$ of 0. Thus, even when the operation speed $\omega$ changes to vibrate to the positive side and the negative side near zero, the braking parameter $\tau$ does not change near the operating speed $\omega$ of 0, and thus it is possible to significantly reduce a sense of discomfort in operation. The sense of discomfort in operation refers to a sense of discomfort such as vibration, for example.

In each of the aforementioned first and second embodiments, before and after switching of control cycles, the braking parameter $\tau$ may not be changed to a predetermined value or more. Thus, it is possible to significantly reduce a sense of discomfort in operation such as vibration due to a large change in the magnitude of the braking parameter $\tau$.

While the four manipulator arms 60 are provided in each of the aforementioned first and second embodiments, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in each of the aforementioned first and second embodiments, the present disclosure is not limited to this. For example, each of the arm portion 61 and the positioner 40 may alternatively include an articulated robot having an axis configuration other than the 7-axis articulated robot. The axis configuration other than the 7-axis articulated robot refers to six axes or eight axes, for example.

While the medical manipulator 1 includes the medical cart 3, the positioner 40, and the arm base 50 in each of the aforementioned first and second embodiments, the present disclosure is not limited to this. For example, the medical manipulator 1 may not include the medical cart 3, the positioner 40, or the arm base 50, but may include only the manipulator arms 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
   a patient-side apparatus including a manipulator arm to which a surgical instrument is attached to a tip end of the manipulator arm;
   an operator-side apparatus including an operation unit to receive an operation of an operator; and
   a controller: wherein
   the operation unit includes a drive to assist the operation;
   the controller is configured or programmed to control the drive to exert a braking force when the operation on the operation unit is decelerated and/or accelerated;
   the controller is configured or programmed to determine a braking parameter of the drive according to an operation speed at which the operation unit is operated, and to control the drive to exert the braking force using the determined braking parameter; and
   the controller is configured or programmed to increase a maximum of an absolute value of the braking parameter during deceleration of the operation to greater than the maximum of the absolute value of the braking parameter during acceleration of the operation.

2. The robotic surgical system according to claim 1, wherein the controller is configured or programmed to, when the operation is decelerated, maintain the braking parameter constant when an absolute value of the operation speed is greater than a first threshold, and decrease an absolute value of the braking parameter as the absolute value of the operation speed decreases when the absolute value of the operation speed is equal to or less than the first threshold.

3. The robotic surgical system according to claim 1, wherein the controller is configured or programmed to, when the operation is decelerated, set the braking parameter to zero when an absolute value of the operation speed is greater than a second threshold, increase an absolute value of the braking parameter as the absolute value of the operation speed decreases when the absolute value of the operation speed is equal to or less than the second threshold and is greater than a third threshold, maintain the braking parameter constant when the absolute value of the operation speed is equal to or less than the third threshold and is greater than a fourth threshold, and decrease the absolute value of the braking parameter as the absolute value of the operation speed deceases when the absolute value of the operation speed is equal to or less than the fourth threshold.

4. The robotic surgical system according to claim 1, wherein the controller is configured or programmed to, when the operation is accelerated, increase an absolute value of the braking parameter as the operation speed increases when an absolute value of the operation speed is less than a fifth threshold, maintain the braking parameter constant when the absolute value of the operation speed is equal to or greater than the fifth threshold and is less than a sixth threshold, decrease the absolute value of the braking parameter as the absolute value of the operation speed increases when the absolute value of the operation speed is equal to or greater than the sixth threshold and is less than a seventh threshold, and set the braking parameter to zero when the absolute value of the operation speed is equal to or greater than the seventh threshold.

5. The robotic surgical system according to claim 1, further comprising:
   a storage to store the braking parameter; wherein
   the controller is configured or programmed to determine the braking parameter based on a table in which the operation speed and the braking parameter are associated with each other.

6. The robotic surgical system according to claim 1, further comprising:
   a braking parameter selector to receive a selection of a magnitude of the braking parameter.

7. The robotic surgical system according to claim 6, wherein the braking parameter selector is provided in the operator-side apparatus.

8. The robotic surgical system according to claim 1, wherein
   the operation unit includes a plurality of rotation axes and a plurality of drives including the drive and provided so as to correspond to the plurality of rotation axes, respectively; and
   the controller is configured or programmed to perform a control to increase the braking force with respect to at least one of the plurality of drives when the operation on the operation unit is decelerated and/or accelerated.

9. An operator-side apparatus to operate a patient-side apparatus including a manipulator arm to which a surgical instrument is attached to a tip end of the manipulator arm, the operator-side apparatus comprising:
   the operator-side apparatus including an operation unit to receive an operation of an operator; and
   a controller; wherein
   the operation unit includes a drive to assist the operation;
   the controller is configured or programmed to control the drive to exert a braking force when the operation on the operation unit is decelerated and/or accelerated;
   the controller is configured or programmed to determine a braking parameter of the drive according to an operation speed at which the operation unit is operated, and to control the drive to exert the braking force using the determined braking parameter; and
   the controller is configured or programmed to increase a maximum of an absolute value of the braking parameter during deceleration of the operation to greater than the maximum of the absolute value of the braking parameter during acceleration of the operation.

10. A control method of a robotic surgical system, the robotic surgical system comprising a patient-side apparatus including a manipulator arm to which a surgical instrument is attached to a tip end of the manipulator arm and an operator-side apparatus including an operation unit to receive an operation of an operator, the operation unit including a drive to assist the operation, the control method comprising:

receiving the operation on the operation unit; and controlling the drive to exert a braking force when the operation on the operation unit is decelerated and/or accelerated, wherein the controlling of the drive to exert the braking force includes determining a braking parameter of the drive according to an operation speed at which the operation unit is operated, and controlling the drive to exert the braking force using the determined braking parameter, and in the determining the braking parameter, a maximum of an absolute value of the braking parameter during deceleration of the operation is greater than the maximum of the absolute value of the braking parameter during acceleration of the operation.

11. The control method of the robotic surgical system according to claim 10, wherein in the determining the braking parameter, when the operation is decelerated, the braking parameter is maintained constant when an absolute value of the operation speed is greater than a first threshold, and an absolute value of the braking parameter is decreased as the absolute value of operation speed decreases when the absolute value of the operation speed is equal to or less than the first threshold.

12. The control method of the robotic surgical system according to claim 10, wherein in the determining the braking parameter, when the operation is decelerated, the braking parameter is set to zero when an absolute value of the operation speed is greater than a second threshold, an absolute value of the braking parameter is increased as the absolute value of the operation speed decreases when the absolute value of the operation speed is equal to or less than the second threshold and is greater than a third threshold, the braking parameter is maintained constant when the absolute value of the operation speed is equal to or less than the third threshold and is greater than a fourth threshold, and the absolute value of the braking parameter is decreased as the absolute value of the operation speed deceases when the absolute value of the operation speed is equal to or less than the fourth threshold.

13. The control method of the robotic surgical system according to claim 10, wherein in the determining the braking parameter, when the operation is accelerated, an absolute value of the braking parameter is increased as the operation speed increases when an absolute value of the operation speed is less than a fifth threshold, the braking parameter is maintained constant when the absolute value of the operation speed is equal to or greater than the fifth threshold and is less than a sixth threshold, the absolute value of the braking parameter is decreased as the absolute value of the operation speed increases when the absolute value of the operation speed is equal to or greater than the sixth threshold and is less than a seventh threshold, and the braking parameter is set to zero when the absolute value of the operation speed is equal to or greater than the seventh threshold.

14. The control method of the robotic surgical system according to claim 10, wherein in the determining the braking parameter, the braking parameter is determined based on a table in which the operation speed and the braking parameter stored in a storage are associated with each other.

15. The control method of the robotic surgical system according to claim 10, further comprising:

receiving a selection of a magnitude of the braking parameter.

16. The control method of the robotic surgical system according to claim 10, wherein the operation unit includes a plurality of rotation axes and a plurality of drives including the drive and provided so as to correspond to the plurality of rotation axes, respectively; and in the controlling of the drive to exert the braking force, a control is performed to increase the braking force with respect to at least one of the plurality of drives when the operation on the operation unit is decelerated and/or accelerated.

* * * * *